(12) United States Patent
Heneveld, Jr. et al.

(10) Patent No.: US 11,986,429 B2
(45) Date of Patent: May 21, 2024

(54) PATIENT TRANSPORT APPARATUS WITH AUTOMATIC HEIGHT ADJUSTMENT

(71) Applicant: Stryker Corporation, Kalamazoo, MI (US)

(72) Inventors: William Ross Heneveld, Jr., Portage, MI (US); Hieu Phan, Portage, MI (US)

(73) Assignee: Stryker Corporation, Kalamazoo, MI (US)

(*) Notice: Subject to any disclaimer, the term of this patent is extended or adjusted under 35 U.S.C. 154(b) by 269 days.

(21) Appl. No.: 17/319,520

(22) Filed: May 13, 2021

(65) Prior Publication Data

US 2021/0353478 A1 Nov. 18, 2021

Related U.S. Application Data

(60) Provisional application No. 63/024,114, filed on May 13, 2020.

(51) Int. Cl.
*A61G 7/018* (2006.01)
*A61G 7/012* (2006.01)
(Continued)

(52) U.S. Cl.
CPC ............ *A61G 7/018* (2013.01); *A61G 7/012* (2013.01); *A61G 7/0524* (2016.11); *G05B 15/02* (2013.01); *A61B 2562/0252* (2013.01); *A61G 2203/10* (2013.01); *A61G 2203/12* (2013.01); *A61G 2203/16* (2013.01); *A61G 2203/20* (2013.01);
(Continued)

(58) Field of Classification Search
CPC .... A61G 7/018; A61G 7/012; A61G 2203/10; A61G 2203/40; A61G 1/04; A61G 2203/12; A61G 2203/16; A61G 2203/20; A61G 2203/22; A61G 1/00; A61G 1/048; A61G 7/015; A61G 7/0524; A61G 2203/30; A61G 2203/32; A61G 2203/34; A61G 2203/36; A61G 2203/38; A61G 2203/42;
(Continued)

(56) References Cited

U.S. PATENT DOCUMENTS 7,398,571 B2  7/2008  Souke et al.
2012/0124744 A1*  5/2012  Hornbach ................ A61G 7/16
                                                    5/613

(Continued)

*Primary Examiner* — Justin C Mikowski
*Assistant Examiner* — Madison Emanski
(74) *Attorney, Agent, or Firm* — Howard & Howard Attorneys PLLC

(57) ABSTRACT

A patient transport apparatus is provided with a lift mechanism to move a litter relative to a base between lift configurations, a user interface with an input control and an indicator, a height sensor, and a controller. The controller is configured to compare signals generated by the height sensor against a value associated with a transport configuration, operate the indicator in a first state when the signal corresponds to the value to communicate to a user that the litter is arranged in the transport configuration, to operate the indicator in a second state when the signal differs from the value to communicate to the user that the litter is arranged in a lift configuration other than the transport configuration, and to drive the lift mechanism to move to the transport configuration in response to the signal being within a predetermined threshold of value upon user disengagement of the input control.

20 Claims, 24 Drawing Sheets

(51) Int. Cl.
*A61G 7/05* (2006.01)
*G05B 15/02* (2006.01)

(52) U.S. Cl.
CPC ...... *A61G 2203/30* (2013.01); *A61G 2203/32* (2013.01); *A61G 2203/40* (2013.01)

(58) Field of Classification Search
CPC ............ A61G 2203/44; A61G 2203/46; G05B 15/02; G16H 40/63; B62D 33/0612
See application file for complete search history.

(56) References Cited

U.S. PATENT DOCUMENTS

| | | | |
|---|---|---|---|
| 2016/0128880 A1* | 5/2016 | Blickensderfer | A61G 1/0256 296/20 |
| 2016/0287454 A1* | 10/2016 | Magill | A61G 1/0262 |
| 2017/0035628 A1 | 2/2017 | Naber et al. | |
| 2017/0143565 A1* | 5/2017 | Childs | A61G 7/053 |
| 2018/0153752 A1* | 6/2018 | Kostic | G06F 3/04817 |
| 2018/0303685 A1 | 10/2018 | Souke et al. | |
| 2018/0303689 A1 | 10/2018 | Souke et al. | |
| 2018/0369039 A1* | 12/2018 | Bhimavarapu | G16H 40/63 |
| 2019/0247254 A1 | 8/2019 | Naber et al. | |
| 2019/0247257 A1 | 8/2019 | Furman et al. | |

* cited by examiner

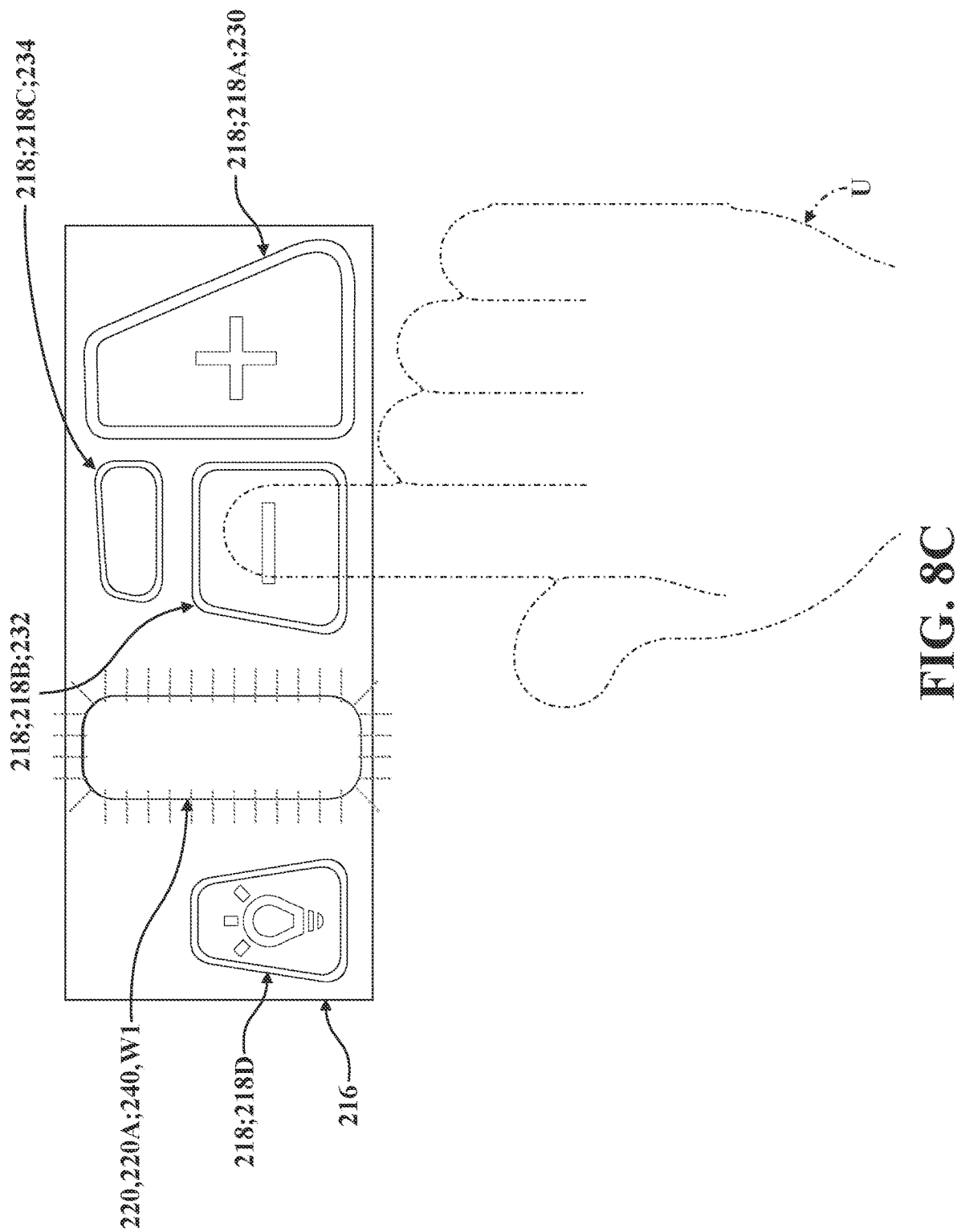

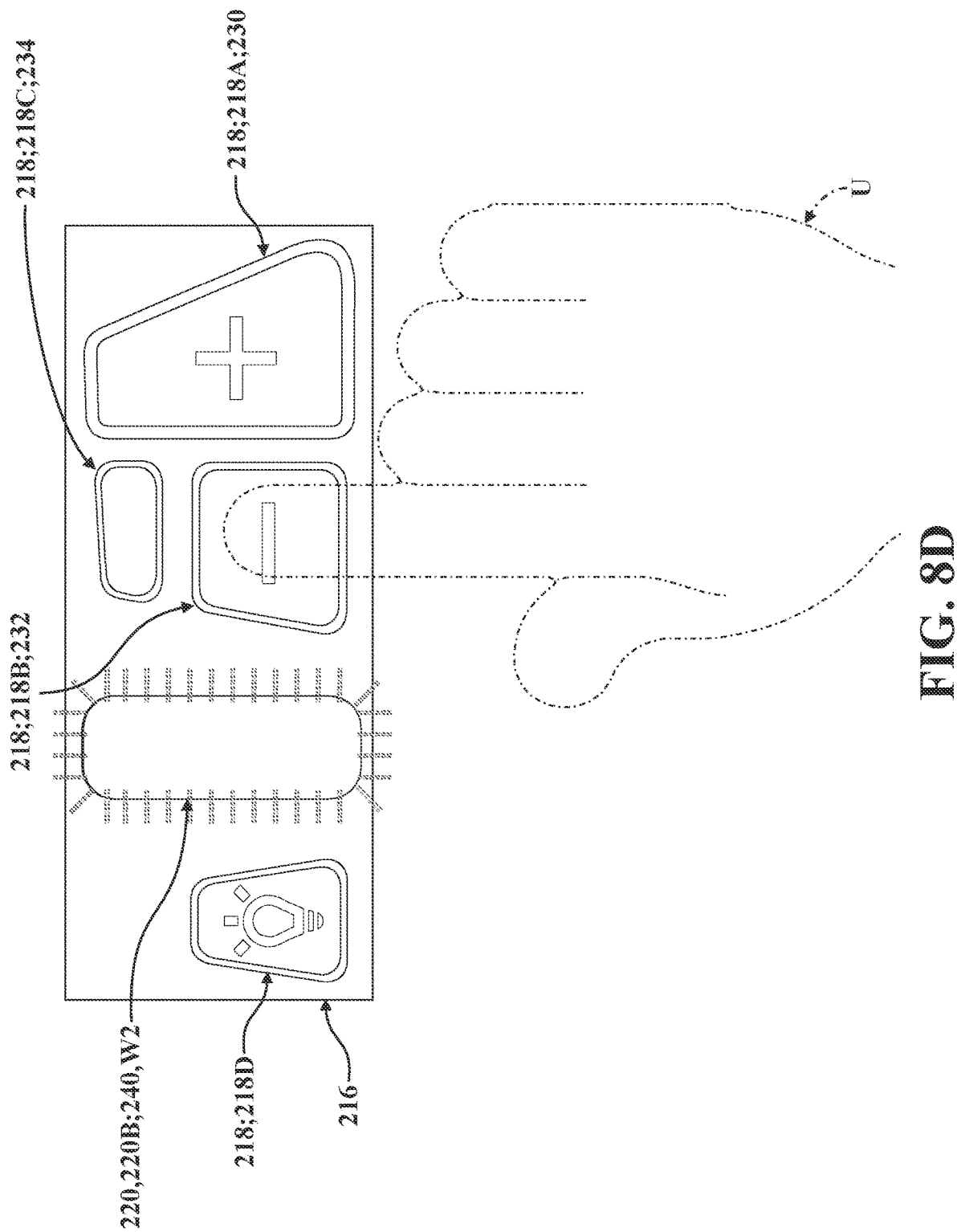

PATIENT TRANSPORT APPARATUS WITH AUTOMATIC HEIGHT ADJUSTMENT

CROSS-REFERENCE TO RELATED APPLICATION

This application claims priority to and all the benefits of U.S. Provisional Patent Application No. 63/024,114, filed on May 13, 2020, the disclosure of which is hereby incorporated by reference in its entirety.

BACKGROUND

Patient transport apparatuses, such as hospital beds, stretchers, cots, tables, wheelchairs, and chairs facilitate care and transportation of patients. Conventional patient transport apparatuses comprise a base, lift mechanism, and a litter comprising a patient support surface upon which the patient is supported. The litter typically comprises several articulable sections, such as a back section and a leg section, to facilitate the care of the patient. Furthermore, the litter can generally be raised and lowered relative to the transport surface to allow for care and transportation of the patient.

During use, the height of the litter may be adjusted based on the needs of the operator of the patient transport apparatus (e.g., a caregiver), such as by raising and/or lowering the litter to a particular height that allows the operator to comfortably manipulate the patient transport apparatus so as to move the patient to a desired location. Alternatively, the operator may adjust the height of the litter based on a procedure to be administered to the patient (e.g., lowering the litter to perform cardiopulmonary resuscitation). For certain types of patient transport apparatuses, a powered lift mechanism may be provided to facilitate adjusting the height of the litter, such as with one or more hydraulic actuators, electric linear actuators, and the like.

While conventional patient transport apparatuses have generally performed well for their intended use, there remains a need in the art for patient transport apparatuses which afford caregivers with the ability to adjust the height of the litter in an consistent, reliable, and straight-forward manner while, at the same time, promoting patient safety during transportation during various scenarios.

BRIEF DESCRIPTION OF THE DRAWINGS

Advantages of the present disclosure will be readily appreciated as the same becomes better understood by reference to the following detailed description when considered in connection with the accompanying drawings wherein:

FIG. 8C is another schematic view of the user interface of FIGS. 8A-8B, shown with the user still engaging the second input control, and with the indicator operating in another state to communicate to the user that the litter is arranged in a transport configuration.

FIG. 8D is another schematic view of the user interface of FIGS. 8A-8C, shown with the user still engaging the second input control, and with the indicator operating in yet another state to communicate to the user that the litter is arranged in a lift configuration lower than the transport configuration.

DETAILED DESCRIPTION

Figure 1:
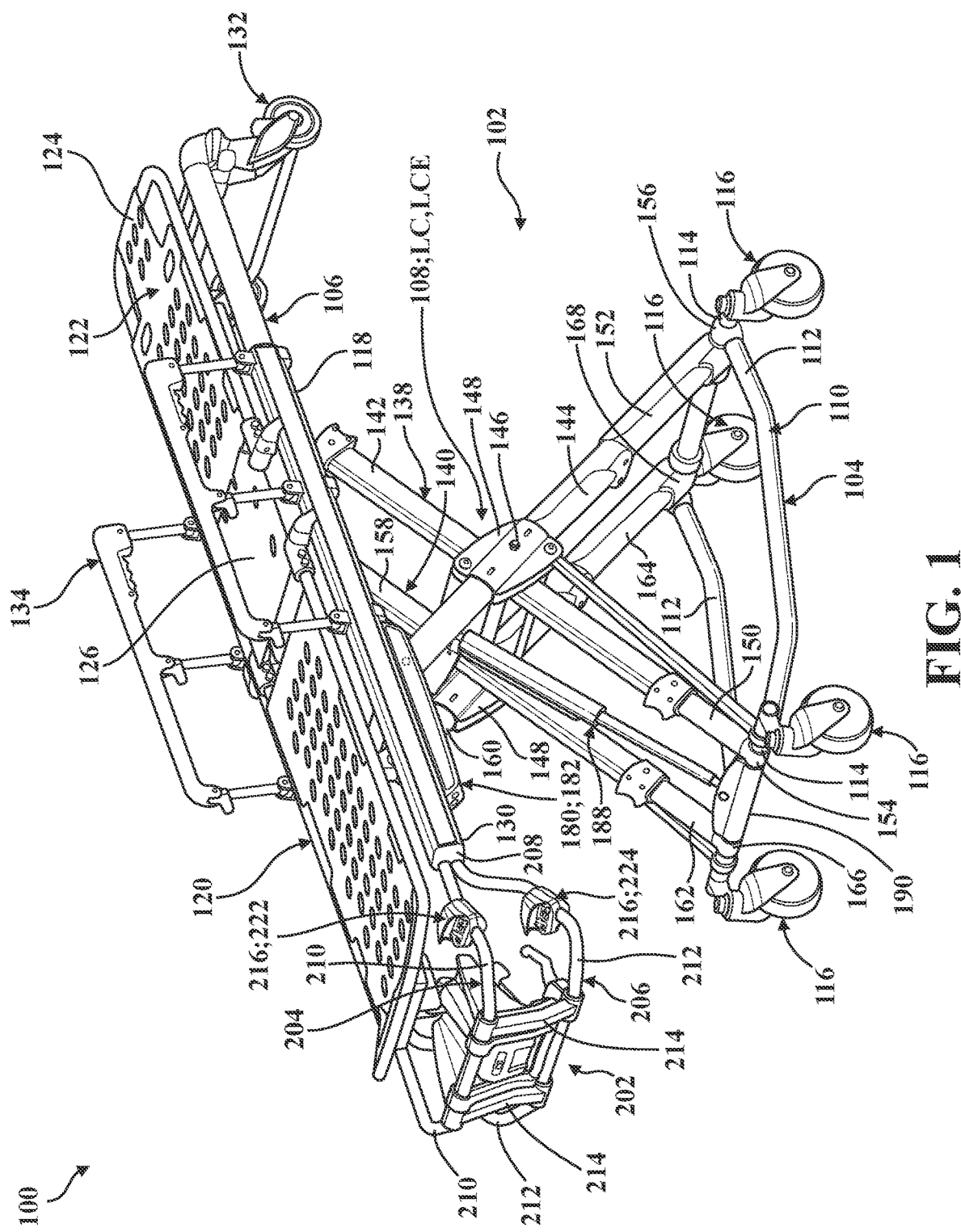
FIG. 1 is a perspective view of a patient transport apparatus shown having a lift mechanism and user interfaces coupled to a litter according to aspects of the present disclosure.

Referring to FIGS. 1-3B, a patient transport apparatus 100 is shown for supporting a patient in a health care and/or transportation setting. The representative aspect of the patient transport apparatus 100 illustrated in FIGS. 1-3B is realized as a cot. In other aspects, however, aspects of the present disclosure could be utilized where the patient transport apparatus 100 is realized as a hospital bed, stretcher, table, wheelchair, chair, or similar apparatus utilized in the transportation and care of a patient.

The patient transport apparatus 100 includes or otherwise defines a support structure 102 to provide support for the patient and facilitate transport. The support structure 102 generally comprises a base 104, a litter 106, and a lift mechanism 108 to move the litter 106 relative to the base 104 as described in greater detail below. In some aspects, the base 104 may include a base frame 110 comprising longitudinal rails 112 and lateral rails 114 interconnected at ends thereof to the longitudinal rails 112 to form a generally rectangular profile. A plurality of caster wheel assemblies 116 are operatively attached to the base 104 adjacent to each corner defined by the rails 112, 114 of the base frame 110. The wheel assemblies 116 may be configured to swivel to facilitate turning or otherwise maneuvering the patient transport apparatus 100. One or more of the wheel assemblies 116 may comprise a swivel locking mechanism (not shown) to prevent the wheel assembly 116 from swiveling when engaged. The wheel assembly 116 may also comprise a wheel brake (not shown) to prevent rotation of the wheel. Other configurations are contemplated.

The litter 106 of the support structure 102 generally comprises a litter frame 118 to which a patient support deck 120 is operatively attached. Here, the patient support deck 120 generally defines a patient support surface 122 configured to support the patient, and comprises various deck sections such as a back section 124, a seat section 126, a leg or foot section 128, and the like which may be articulable relative to each other and/or relative to the litter frame 118 to facilitate positioning the patient in different positions. In some aspects, a mattress (not shown) may be provided on the patient support deck 120 to define a secondary patient support surface. The litter frame 118 of the litter 106 may comprise hollow side rails 130 that extend longitudinally along the patient support surface 122. The litter 106 may further comprise or otherwise support loading wheels 132 extending from the litter frame 118 proximate the back section 124 to facilitate loading and unloading of the patient transport apparatus 100 from a vehicle. For example, the loading wheels 132 may be positioned and configured to facilitate loading and unloading the patient transport apparatus 100 into an ambulance.

Hand rails 134 may extend from opposing sides of the litter frame 118 to provide egress barriers for the patient on the patient support surface 122. The hand rails 134 may also be utilized by a user U, such as an emergency medical technician (EMT) or other medical professional, to move or manipulate the patient transport apparatus 100. The hand rails 134 may comprise a hinge, pivot or similar mechanism to allow the rails 134 to be folded or stored at or below the plane of the patient support surface 122. A vertical support member 136 (see FIG. 3A) may also be attached to the litter frame 118. The vertical support member 136 may be configured to hold a medical device or medication delivery system, such as a bag of fluid to be administered via an IV. The vertical support member 136 may also be configured for the operator of the patient transport apparatus 100 to push or pull on the vertical support member 136 to manipulate or move the patient transport apparatus 100.

As noted above, the lift mechanism 108 is provided to facilitate arranging the litter 106 relative to the base 104. More specifically, the lift mechanism 108 is configured to move the litter 106 relative to the base 104 between a plurality of lift configurations LC including a fully-extended configuration LCE (see FIG. 3A), a fully-retracted configuration LCR (see FIG. 3B), and one or more transport configurations LCT (see FIG. 3C) between the fully-extended configuration LCE and the fully-retracted configuration LCR. In the representative aspect illustrated herein, the lift mechanism 108 interconnects the base 104 and the litter 106 to facilitate raising and lowering of the litter 106 relative to a transport surface (e.g., a floor surface). As will be appreciated from the subsequent description below, the transport configuration LCT may be defined in a number of different ways. For the illustrative purposes of clarity and consistency, the transport configuration LCT will be understood to be defined as a "standard height" of the litter 106 relative to the base 104 which promotes safe operation of the patient transport apparatus 100 during normal use conditions. However, the transport configuration LCT may be adjusted based, among other things, on user preference, municipal or other regulatory guidelines, and the like. Other configurations are contemplated.

The lift mechanism 108 may be manipulated to adjust the height of the litter 106 as described in greater detail below. While moving between the plurality of lift configurations LC, the lift mechanism 108 may move either the base 104 or the litter 106 relative to the other of the litter 106 or the base 104 depending on how the patient transport apparatus 100 is supported during use. For instance, in FIGS. 3A-3C, the patient transport apparatus 100 is supported at the base 104 on the ground. In other instances, the patient transport apparatus 100 may be supported at the litter 106, such as when the patient transport apparatus 100 is being unloaded/loaded into an emergency response vehicle. In instances where the patient transport apparatus 100 is supported at the litter 106, the lift mechanism 108, while moving between the plurality of lift configurations LC, moves the base 104 relative to the litter 106. In instances where the patient transport apparatus 100 is supported at the base 104, while moving between the plurality of lift configurations LC, the lift mechanism 108 moves the litter 106 relative to the base 104.

In the illustrated aspect, the lift mechanism 108 includes side-by-side oriented first and second "X" frame assemblies 138, 140. The first frame assembly 138 comprises first and second left-side upper frame members 142, 144 interconnected together adjacent to their midpoints via a pivot axle 146 extending through a bracket 148. In the illustrated aspect, the first and second left-side upper frame members 142, 144 are each hollow and telescopingly receive therein respective first and second left-side lower frame members 150, 152, which are supported for movement into and out of the respective first and second left-side upper frame members 142, 144. As is best shown in FIG. 1, the distal end of the first left-side lower frame member 150 is secured via a first left-side connection 154 to the lateral rail 114 at the left-side foot end of the base 104, and the distal end of the second left-side lower frame member 152 is connected via a second left-side connection 156 to the lateral rail 114 at the right-side head end of the base 104.

The second frame assembly 140 is similarly constructed, and comprises first and second right-side upper frame members 158, 160 interconnected together adjacent to their midpoints via the pivot axle 146 extending through another bracket 148. While the axle 146 is illustrated to extend laterally between the first and second frame assemblies 138, 140, it is to be understood that separate axles 24 can, if desired, be employed. Here too, the first and second right-side upper frame members 158, 160 are each hollow and telescopingly receive therein respective first and second right-side lower frame members 162, 164, which are supported for movement into and out of the respective first and second right-side upper frame members 158, 160. The distal end of the first right-side lower frame member 162 is secured via a first right-side connection 166 to the lateral rail 114 at the right-side foot end of the base 104, and the distal end of the second right-side lower frame member 164 is connected via a second right-side connection 168 to the lateral rail 114 at the right-side head end of the base 104. While the patient transport apparatus 100 illustrated throughout the drawings comprises a support structure 102 with a lift mechanism 108 comprising first and second frame assemblies 138, 140, it will be appreciated that other configurations are contemplated, and the patient transport apparatus 100 may comprise a support structure 102 and base 104 with a pair of front and rear folding leg members in some aspects (e.g., realized as a "roll-in cot").

The proximal ends P of the second left-side upper frame member 144 and the second right-side upper frame member 160 are slidably engaged with respective brackets 170 (only one shown) attached to the underside of the side rails 130 of the litter frame 118. Each bracket 180 comprises a respective slot or track 182 configured to allow the proximal ends P of the second left-side upper frame member 144 and the second right-side upper frame member 160 to travel along the tracks 182 as the lift mechanism 108 is manipulated move the litter 106 relative to the base 104 between the plurality of lift configurations LC. The configuration or shape of the track 182 may be configured to orient the litter 106 at a particular angle as the lift mechanism 108 is raised and/or lowered. For example, the track 182 may be configured to be straight, or it may comprise one or more bends or curves, creating an S-like shape. In some aspects, the shape of track 182 may be configured to keep the litter 106 approximately level as the litter 106 is raised or lowered between certain lift configurations LC (compare FIGS. 3B-3C). The track 182 may also be configured to tilt or angle the patient support surface 122 of the litter 106 so that either the head or leg end of the litter 106 is elevated relative to the opposing end of the litter 106 in certain lift configurations (see FIG. 3A). For example, the track 182 may be configured to elevate the head end of the patient support surface 122 when raised to the fully-extended configuration LCE to assist in loading and unloading the patient transport apparatus 100 in a vehicle. An outer surface of the bracket 180 may comprise markings, such as a ruler, configured to display the height of the litter 106 in the present position. For example, as the height of the litter 106 is adjusted by the user U and the proximal ends P of the second left-side upper frame member 144 and the second right-side upper frame member 160 slide along the tracks 182, a pin may move along the ruler to indicate the height of the litter 106. Other configurations are contemplated.

In the representative aspect illustrated herein, the patient transport apparatus 100 employs a control system 184 with a controller 186 (see FIG. 2) to effect operation of the lift mechanism 108 by, among other things, driving one or more actuators 188 (see FIGS. 1, 2, and 4) configured to manipulate the first and second frame assemblies 138, 140 to move the litter 106 relative to the base 104 between the lift configurations LC. The control system 184. The controller 186, and the actuator 188 will each be described in greater detail below.

Figure 4:
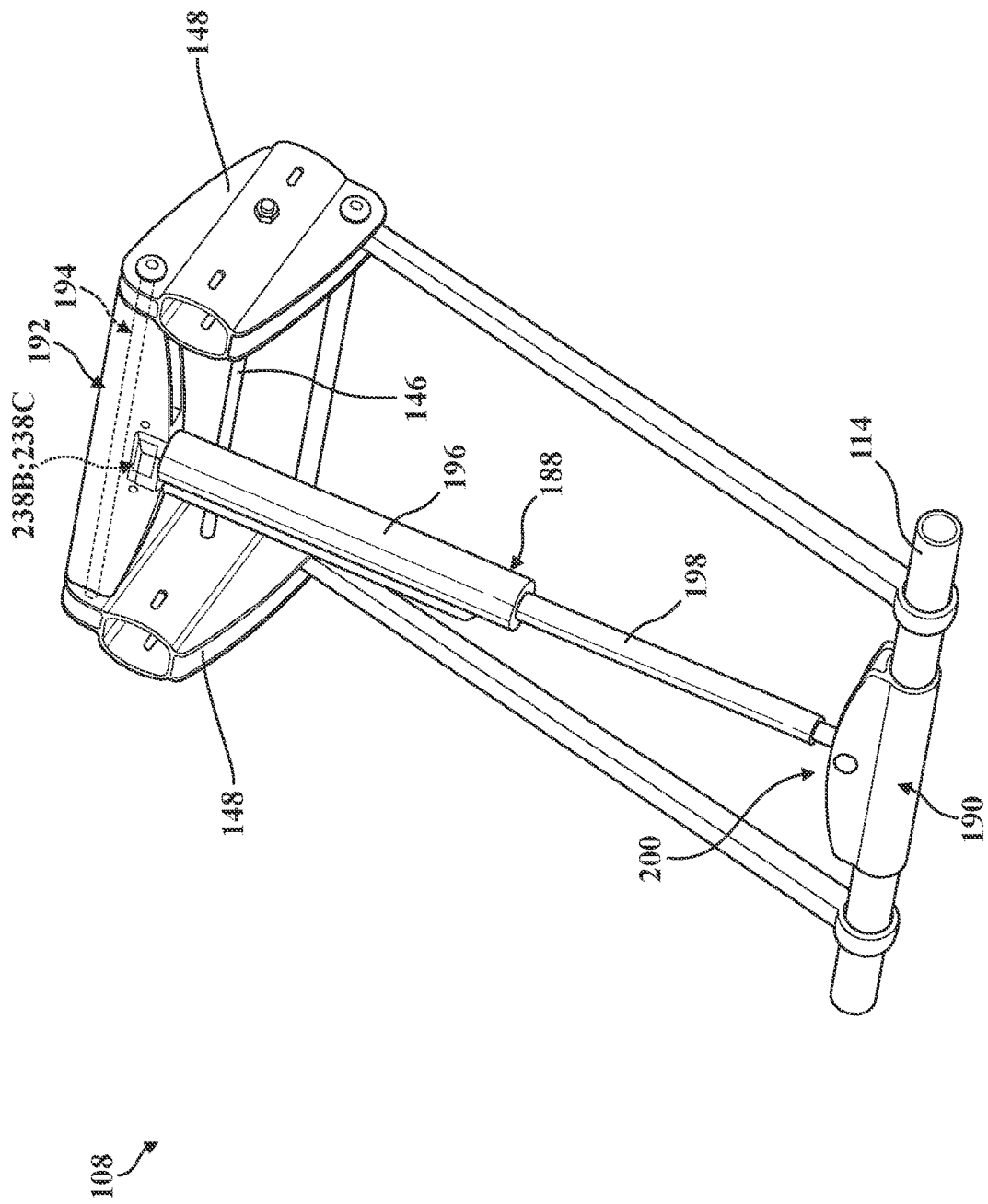
FIG. 4 is a perspective view of an aspect of the lift mechanism of the patient transport apparatus of FIG. 1.

As is best depicted in FIG. 4, in the representative aspect illustrated herein, a lower support 190 is supported by the lateral rail 114, and an upper support 192 is supported by a shaft 194 that is connected to and extends between the respective brackets 148 of the first and second frame assemblies 138, 140. The shaft 194 is connected to each bracket 148 by a respective fastener (not shown in detail). Here in this aspect, the actuator 188 is realized as a hydraulic linear actuator which is connected to and extends between the upper and lower supports 190, 192. While a single, hydraulically-actuated, linear actuator 188 is employed in the representative aspect illustrated herein, those having ordinary skill in the art will appreciate that actuators 188 of various styles, types, and/or configurations could be utilized without departing from the scope of the present disclosure. By way of non-limiting example, one or more linear and/or rotary actuators 188 could be utilized in some aspects, one or more of which could be driven via the control system 184 using various combinations of electrical, hydraulic, and/or pneumatic components, systems, and the like. Other configurations are contemplated.

In the representative aspect illustrated herein, the actuator 188 comprises a cylinder housing 196 fastened to the upper support 192, and a reciprocal rod 198 having a piston (not illustrated) at one end thereof located within the cylinder housing 196. The distal end of the reciprocal rod 198 is connected in a conventional manner by a joint 200 to the lower support 190. Here, the joint 200 allows pivotal movement about two orthogonally related axes (e.g., as a "universal joint"). Extension and retraction of the reciprocal rod 198 facilitates movement of the litter 106 relative to the base 104 between the lift configurations LC. The Applicant has described aspects of these types of lift mechanisms 108 in U.S. Pat. No. 7,398,571 entitled "Ambulance Cot and Hydraulic Elevating Mechanism Therefor," U.S. Patent Application Publication No. 2018/0303689 A1 entitled "Emergency Cot With a Litter Height Adjustment Mechanism," and U.S. Patent Application Publication No. 2018/0303685 A1 entitled "Patient Handling Apparatus with Hydraulic Control System," the disclosures of each of which are hereby incorporated by reference in their entirety. However, as noted above, other configurations are contemplated.

Figure 5:
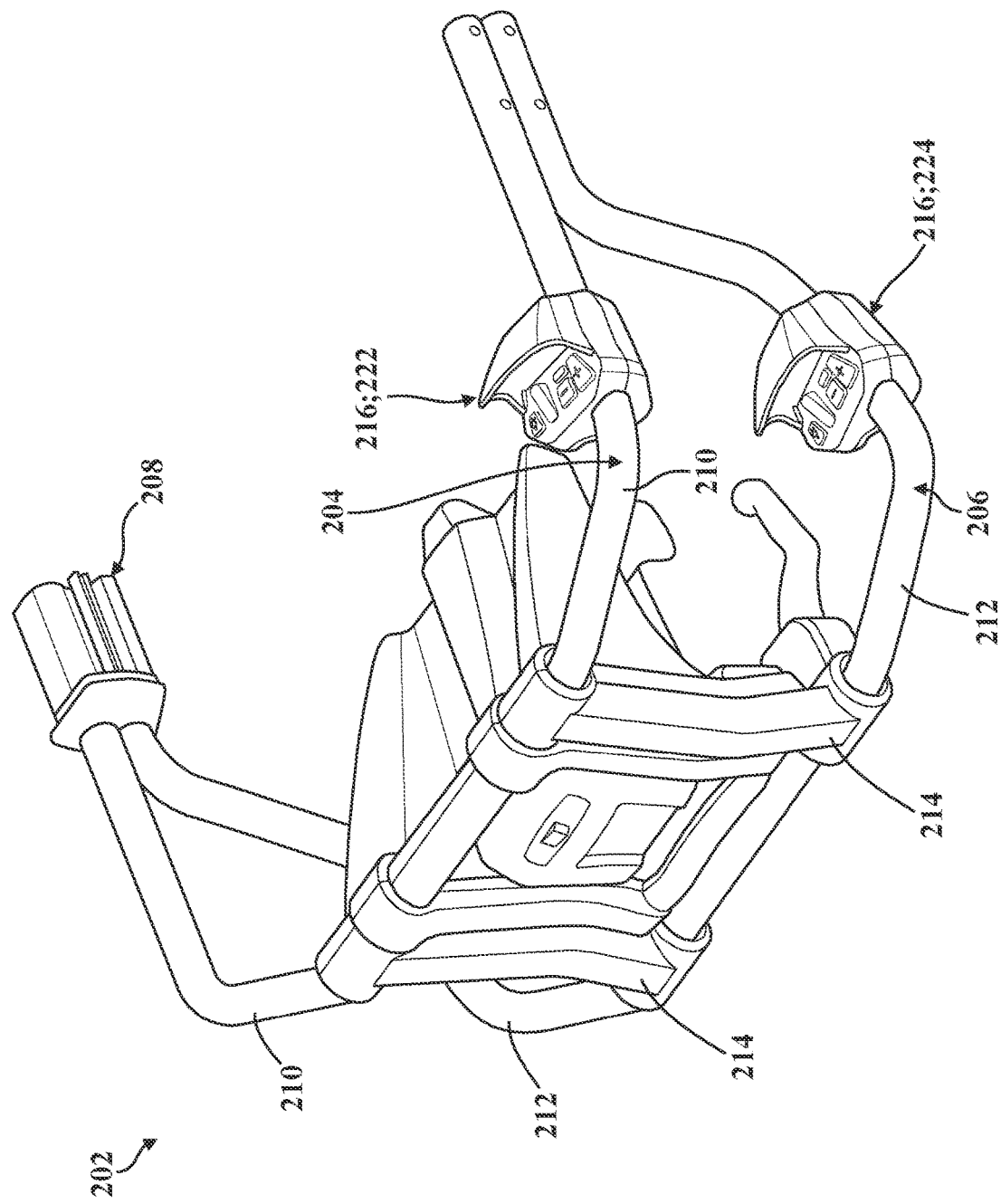
FIG. 5 is a perspective view of portions of the litter and the user interfaces of the patient transport apparatus of FIG. 1.

A foot end lift handle mechanism 202 is illustrated in FIG. 5 and comprises vertically-spaced first and second frame members 204, 206 which each have a generally U-shaped profile. The ends of each of the first and second frame members 204, 206 are joined together by a coupler 208 (only one shown in FIG. 5). Each coupler 208 may be telescopingly affixed inside of the leg end of the respective side rails 130 (see FIG. 1). Further, the ends of the second frame member 206 diverge away from the legs of the first frame member 204 so as to provide vertically-spaced first and second hand grip areas 210, 212 on the respective first and second frame members 204, 206. Spacer brackets 214 may be connected to opposing portions of each of the first and second frame members 204, 206 to maintain the vertical spacing between the first and second hand grip areas 210, 212. A fastener such as a bolt or a pin (not shown) may be utilized to facilitate securing the couplers 208 to the interior of each of the respective side rails 130.

As is described in greater detail below in connection with FIGS. 2, 5, and 7A-8F, the control system 184 includes a user interface, generally indicated at 216, which comprises input controls 218A, 218B, 218C, 218D arranged for engagement by the user U to operate or otherwise control various aspects of the patient transport apparatus 100 (e.g., the lift mechanism 108), as well as one or more indicators 220 operable between various different states 220A, 220B, 220C to communicate information to the user U. In the representative aspects illustrated herein, and as is best depicted in FIG. 5, one user interface 216 is supported in an upper housing 222 coupled to the first frame member 204 of the foot end lift handle mechanism 202, and another user interface 216 is supported in a lower housing 224 coupled to the second frame member 206. Here, the upper and lower housings 222, 224 provide the user U with the ability to access the input controls 218A, 218B, 218C, 218D and view the indicator 220 from two different locations that may be selectively utilized by the user U depending, for example, on which lift configuration LC the litter 106 is arranged in relative to the base 104. However, it will be appreciated that additional user interfaces 216 (or a single user interface 216), with the same or different configurations, input controls, and/or indicators, may be provided in some aspects. Other configurations are contemplated.

The patient transport apparatus 100 employs the controller 186 to, among other things, operate the actuator 188 of the lift mechanism 108 via one or more user interfaces 216. To this end, the controller 186 generally comprises one or more processors 226 and a non-transitory storage medium or other suitable type of memory 228 onto which data, information, programs, and/or instructions for execution by the processor 226 are stored. More specifically, and in some aspects, the controller 186 may comprise various arrangements of microprocessors, microcontrollers, field programmable gate arrays, systems on a chip, discrete circuitry, and/or other suitable hardware, software, or firmware that is capable of carrying out the functions described herein. The controller 186 may be carried on-board the patient transport apparatus 100 (as shown), or may be remotely located. Power to the actuator 188 and/or the controller 186 may be provided by a battery power supply and/or an external power source. The controller 186 is coupled to the actuator 188 in a manner that allows the controller 186 to control the actuator 188. The controller 186 may communicate with the actuator 188 via wired or wireless connections to perform one or more desired functions.

As noted above, one or more user interfaces 216 comprise input controls 218A, 218B, 218C, 218D arranged for engagement by the user U. In some aspects, a first input control 218A comprises a plus (+) button 230 arranged for engagement by the user U to move the litter 106 toward the fully-extended configuration LCE, and a second input control 218B comprises a minus (−) button 232 arrangement for engagement by the user U to move the litter 106 toward the fully-retracted configuration LCR. Here, the controller 186 is configured to drive the lift mechanism 108 (e.g., by controlling an electric motor operating a hydraulic pump in fluid communication with the actuator 188) toward the fully-extended configuration LCE in response to user U engagement with the first input control 218A (e.g., with the plus button 230), and to drive the lift mechanism 108 toward the fully-retracted configuration LCR in response to user U engagement with the second input control 218B (e.g., with the minus button 232).

In some aspects, and as is described in greater detail below, an automatic input control 218C comprises a transport button 234 arranged for engagement by the user U, and the controller 186 is further configured to drive the lift mechanism 108 to move to the transport configuration LCT in response to user engagement with the automatic input control 218C. The Applicant has described this type of functionality in U.S. Patent Application Publication No. 2019/0247254 A1 entitled "Patient Transport Apparatus with Defined Transport Height," the disclosure of which is hereby incorporated by reference in its entirety. However, as noted above, other configurations are contemplated. One or more of the user interfaces 216 may also comprise additional buttons and/or input controls 218 configured to manipulate the litter 106 and/or patient support surface 122. In some aspects, and as is depicted schematically in FIG. 2, the user interface 216 comprises an area light input control 218D arranged for user engagement U to activate an area light module 236 coupled to the patient transport apparatus 100 and arranged to selectively emit visible light toward the ground or other adjacent areas. Other configurations are contemplated.

As will be appreciated from the subsequent description below, the user interfaces 216, input controls 218A, 218B, 218C, 218D, and/or indicators 220 could be configured in a number of different ways without departing from the scope of the present disclosure. Here, by way of non-limiting example, the input controls 218A, 218B, 218C, 218D could be realized with various types of switches, buttons, sensors, and the like which generate signals that can be communicated, transmitted, or otherwise interpreted by the controller 186 (e.g., via wired or wireless electrical communication) to effect operation and control of the patient transport apparatus 100. In some aspects, the user interface 216 could be realized as a "touchscreen" interface, with input controls 218A, 218B, 218C, 218D defined as virtual "buttons" on a graphical user interface GUI, and with indicators 220 defined as icons, graphics, alerts, symbols, and the like presented on the graphical user interface GUI (not shown, but generally known in the art). Other configurations are contemplated.

The patient transport apparatus 100 may further comprise one or more sensors 238 coupled to the controller 186. By way of non-limiting example, the sensors 238 may be optical sensors, ultrasonic sensors, laser sensors, proximity sensors, pressure sensors, load cells, strain gauges, location sensors, motion sensors, orientation sensors, and/or other suitable sensors for carrying out the functions described herein. The sensors 238 may be configured to detect (and communicate with the controller 186 about) a plurality of characteristics related to the configuration, position, and/or utilization of the patient transport apparatus 100. The sensors 238 and/or the controller 186 may be configured to determine information to generate control commands (output signals) used to manipulate the patient transport apparatus 100 based on a predefined set of rules and/or algorithms for interpreting signals from the sensors 238. The information may be stored in the memory 228. Various types of sensors 238, and how they can be utilized via the controller 186 to operate the patient transport apparatus 100, will be described in n greater detail below.

Figure 2:
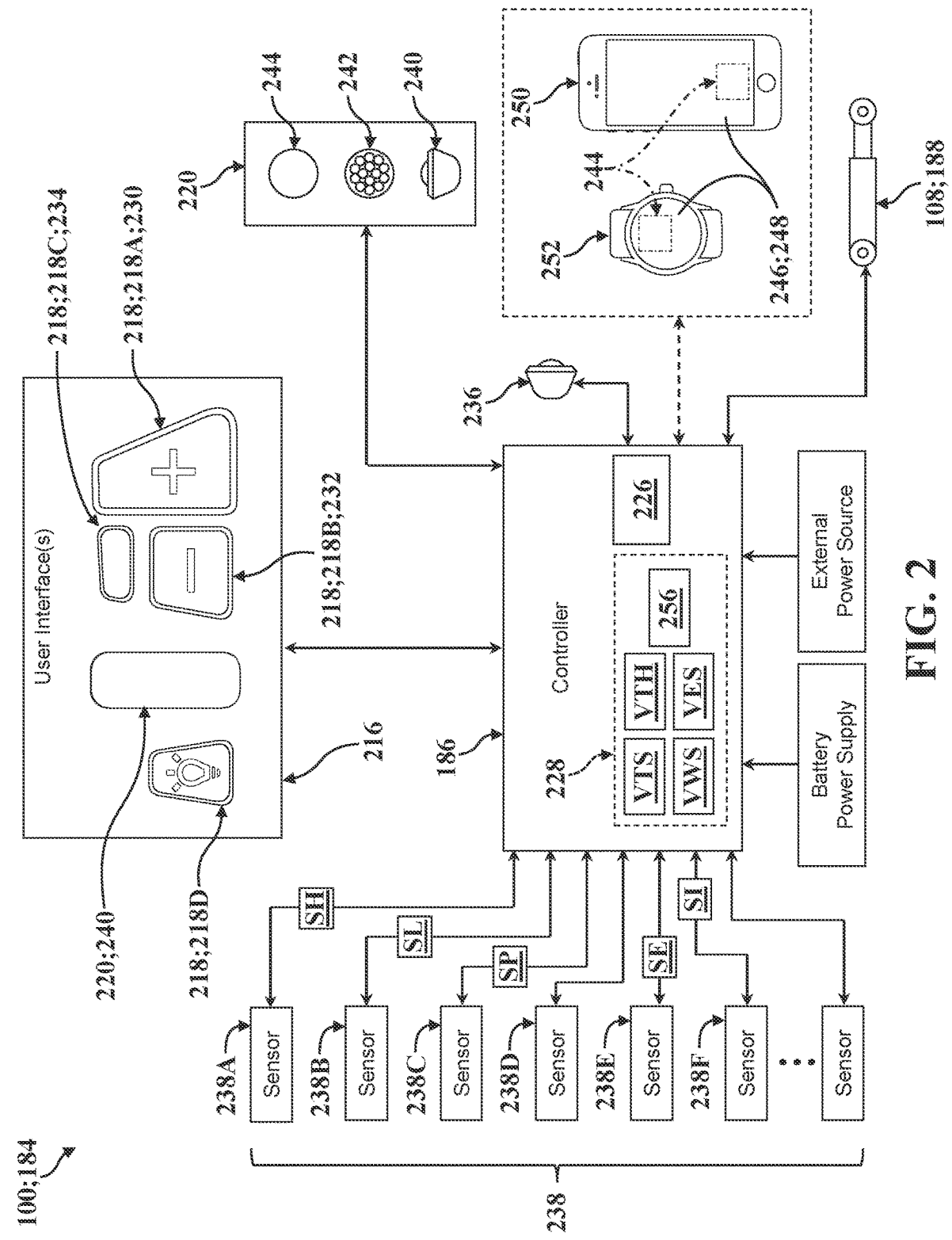
FIG. 2 is a schematic diagram of a control system of the patient transport apparatus of FIG. 1.

In some aspects, and as is depicted schematically in FIG. 2, the patient transport apparatus 100 comprises a height sensor 238A to generate a signal SH indicative of the arrangement of the patient support surface 122 (or another component of the litter 106) relative to the base 104 between the plurality of lift configurations LC. To this end, the height sensor 238A may comprise one or more discrete components coupled to the litter 106, the base 104, the actuator 188, or to any other suitable location on the patient transport apparatus 100 sufficient to measure or otherwise determine the height of the litter 106 relative to the base 104. For example, a laser sensor, a proximity sensor, or an optical sensor may be attached to the underside of the litter 106 and configured to detect/measure the distance between the litter 106 and the base 104. The distance measured by the sensor may be communicated to the controller 186 and/or determined by the controller 186.

In some aspects, the height sensor 238A may be realized with one or more Hall effect sensors operatively attached to the actuator 188 to measure or otherwise determine how far the actuator 188 has been moved (e.g. movement of the reciprocal rod 198), with the controller 186 configured to determine the height of the patient support surface 122 based on the displacement of the actuator 188. In some aspects, one or more sensors may be placed in the track 182 to detect a position of one or more of the proximal ends of the frame members 142, 144 sliding along the tracks 182 wherein the controller 186 is configured to indirectly determine the height of the patient support surface 122 based on a predefined relationship of height to the positions of the proximal ends in the tracks 182. The Applicant has described aspects of this type of height sensor 238A in U.S. Pat. No. 7,398,571 entitled "Ambulance Cot and Hydraulic Elevating Mechanism Therefor," previously referenced.

Other suitable height sensors 238A may comprise various types and configurations of one or more Hall Effect sensors, proximity sensors, reed switches, optical sensors, ultrasonic sensors, liquid level sensors, linear variable displacement transformer (LVDT) sensors, linear potentiometers, magnetostrictive sensors, and the like. In some aspects, the height sensor 238A may be similar to as is disclosed in U.S. Patent Application Publication No. 2019/0247257 A1 entitled "Techniques for Determining a Pose of a Patient Transport Apparatus," the disclosure of which is hereby incorporated by reference in its entirety. Other configurations are contemplated.

Referring now to FIGS. 2, 6A, and 7A-7F, as noted above, one or more of the user interfaces 216 employ the indicator 220 to communicate information to the user U. In some aspects, the indicator 220 is operable between a first state 220A and a second state 220B different from the first state 220A. The controller 186 is connected to the lift mechanism 108, the height sensor 238A, and the user interface 216, and comprises one or more processors 226 and the memory 228 (non-transitory storage medium) having stored thereon instructions that when executed by the one or more processors 226 are configured to effect control of the patient transport apparatus 100. In this way, the controller 186 is configured to compare the signal SH generated by the height sensor 238A against a transport signal value VTS associated with the transport configuration LCT.

Figure 6A:
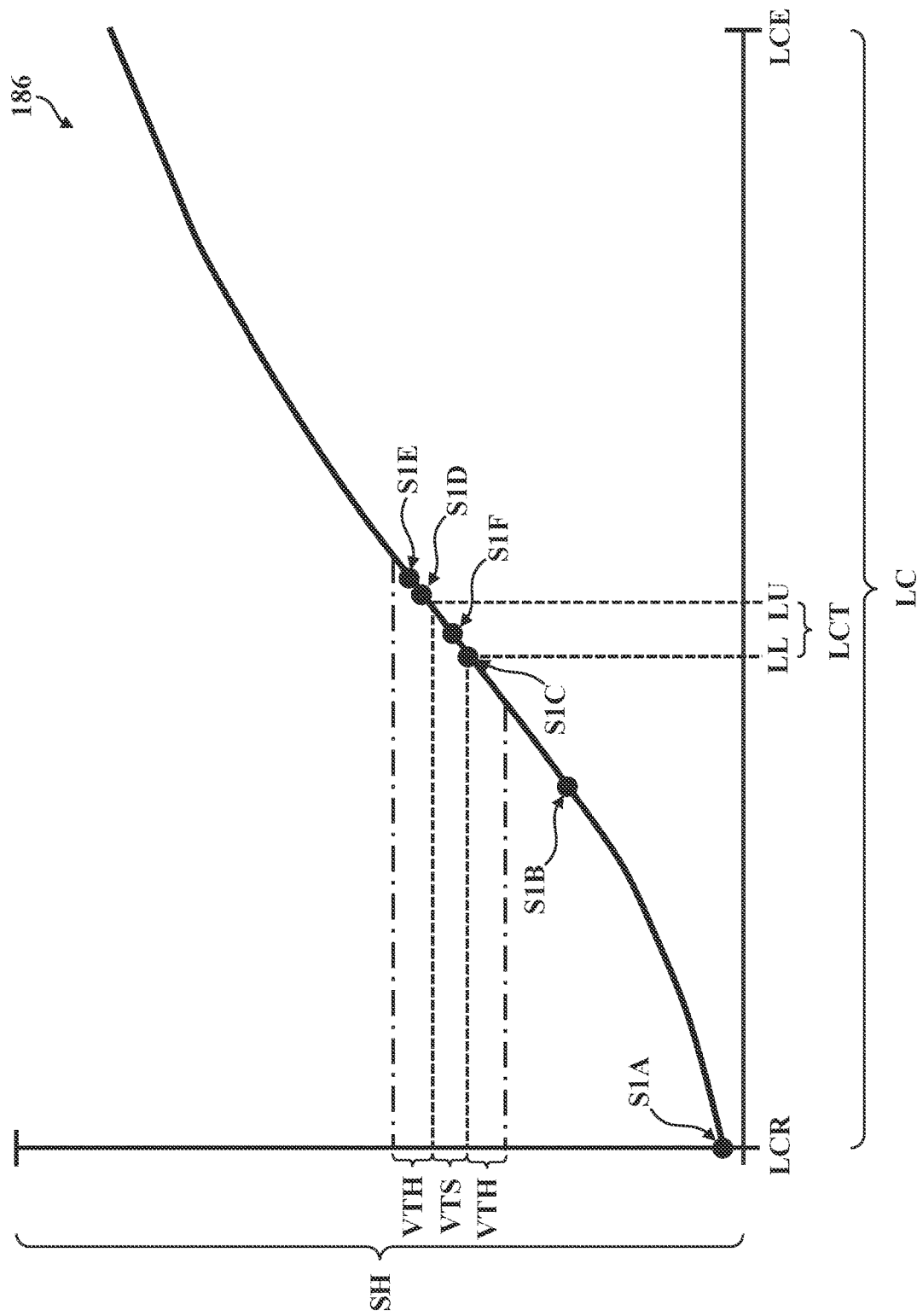
FIG. 6A is a graphical representation of various lift configurations of the patient transport apparatus of FIG. 1 plotted against height sensor signal data to illustrate transport configurations between a fully-retracted configuration and a fully-extended configuration.

Put differently, and as is depicted in graphical form in FIG. 6A, the signal SH generated by the height sensor 238A (shown along the vertical axis in FIG. 6A) may correspond to the "current" (or, in some aspects "commanded") lift configuration LC of the litter 106 between the fully-extended configuration LCE and the fully-retracted configuration LCR (shown along the horizontal axis in FIG. 6A). It will be appreciated that FIG. 6A illustrates an exemplary illustration of the relationship between the plurality of litter configurations LC and the corresponding signal SH that may be generated by the height sensor 238A. In some aspects, the transport configuration LCT may be defined by a plurality of transport configurations LCT between the fully-retracted configuration LCR and the fully-extended configuration LCT. Here, for example, the transport configuration LCT may comprise a "range" of lift configurations LC defined by an upper limit LU and an lower limit LL (see FIG. 6A). Other configurations are contemplated.

The controller 186 is configured to operate the indicator 220 in the first state 220A (see FIGS. 7C and 7F; see also FIGS. 8C and 8F) when the signal SH generated by the height sensor 238A corresponds to the transport signal value VTS to communicate to the user U that the litter 106 is arranged in the transport configuration LCT, and to operate the indicator 220 in the second state 220B (see FIGS. 7A-7B and FIGS. 7D-7E) when the signal SH generated by the height sensor 238A differs from the transport signal value VTS to communicate to the user U that the litter 106 is arranged in one of the plurality of lift configurations LC other than the transport configuration LCT. The controller 186 is also configured to drive the lift mechanism 108 (e.g., by controlling the actuator 188) to automatically move to the transport configuration LCT in response to the signal SH generated by the height sensor 238A being within a predetermined threshold VTH of the transport signal value VTS upon user U disengagement of the input control 218.

While user interfaces 216 may comprise various input controls 218 and/or indicators 220 as described in greater detail below, one exemplary implementation of the "automatic height correction" effected by the controller 186 introduced above is illustrated by successively comparing FIGS. 7A-7F with reference to FIG. 6A. In the representative aspect illustrated in FIG. 7A, the user interface 216 is shown having the first input control 218A (the plus button 230), the second input control 218B (the minus button 232), and the automatic input control 218C (the transport button 234) arranged for engagement by the user U. In this representative aspect, the indicator 220 comprises a light source 240, such as one or more single or multi-color light-emitting diodes (LEDs). Here, the first state 220A of the indicator 220 is further defined as light emission via the light source 240, and the second state 220B of the indicator 220 is further defined as an absence of light emission via the light source 240. However, and as will be appreciated from the subsequent description below, other configurations are contemplated, and other and/or additional types of indicators 220 could be utilized without departing from the scope of the present disclosure. In some aspects, the first state 220A of the indicator 220 may be further defined as light emission via the light source 240 at a first wavelength W1 (e.g., blue visible light), and the second state 220B of the indicator 220 may be further defined as light emission via the light source 240 at a second wavelength W2 (e.g., another color of visible light) different from the first wavelength W1. Here too, it will be appreciated that other configurations are contemplated.

Figure 3A:
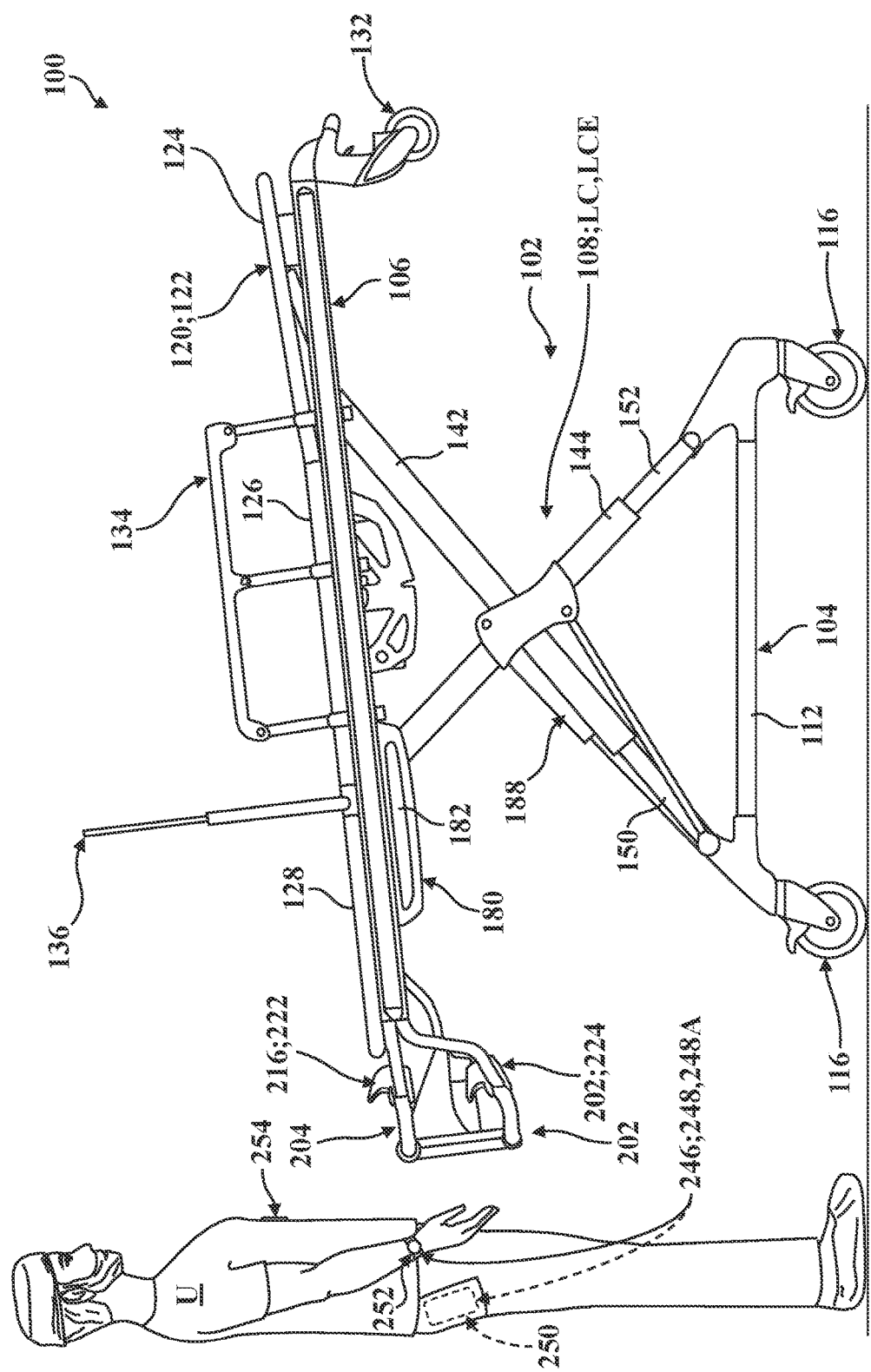
FIG. 3A is a side view of the patient transport apparatus of FIG. 1, shown arranged in a fully-extended configuration.
Figure 3B:
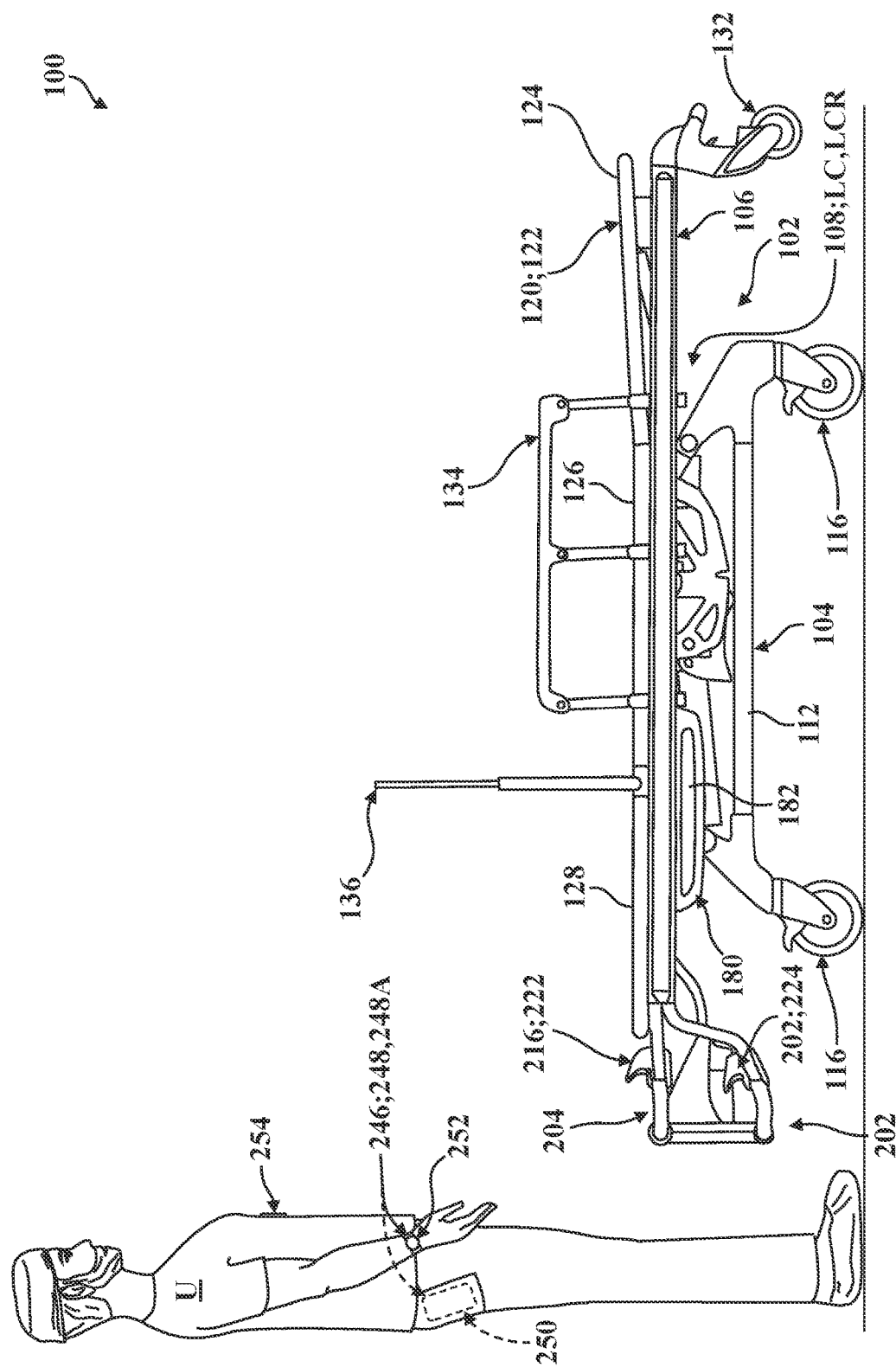
FIG. 3B is another side view of the patient transport apparatus of FIG. 3A, shown arranged in a fully-retracted configuration.
Figure 3C:
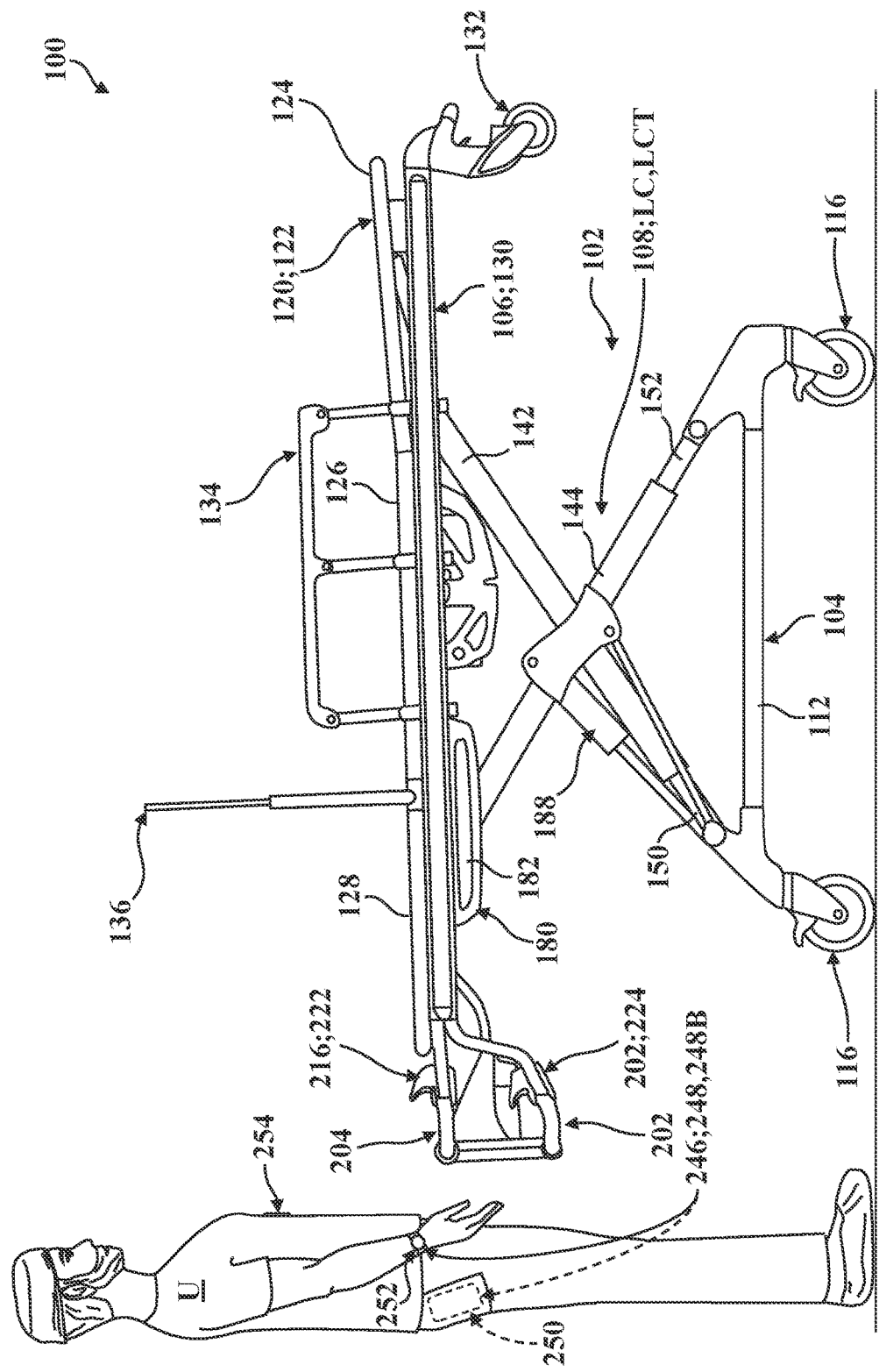
FIG. 3C is another side view of the patient transport apparatus of FIGS. 3A-3B, shown arranged in a transport configuration.
Figure 7A:
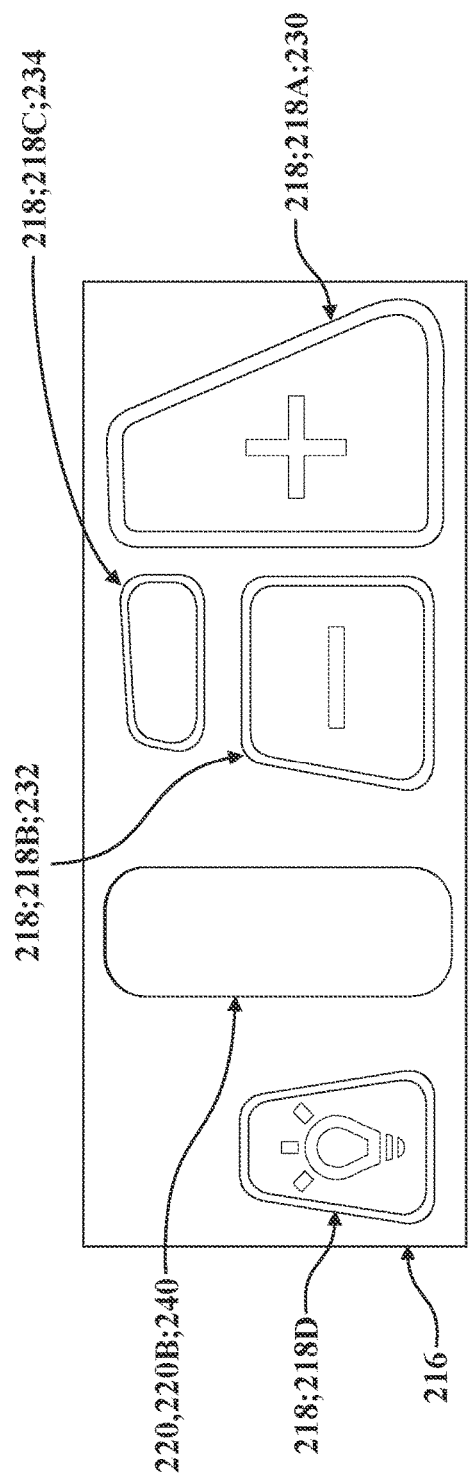
FIG. 7A is a schematic view of a user interface of the patient transport apparatus of FIGS. 1-6D, shown having input controls and an indicator according to aspects of the present disclosure.

For illustrative purposes, FIG. 7A may represent a use scenario where the user U is about to utilize the user interface 216 to "raise" the patient transport apparatus 100 from the fully-retracted configuration LCR depicted in FIG. 3B, and desires to place the litter 106 in the transport configuration LCT depicted in FIG. 3C. To this end, the user U could engage and the automatic input control 218C (e.g., the transport button 234), whereby the controller 186 would evaluate the signal SH from the height sensor 238A to determine the "current" lift configuration LC of the litter 106 (here in this example, the fully-retracted configuration LCR), and subsequently drive the lift mechanism 108 (e.g., by powering the actuator 188) automatically toward the transport configuration LCT so long as the user U continued to engage the automatic input control 218C. Once the lift mechanism 108 had arranged the litter 106 in the transport configuration LCT as determined via the height sensor 238A (e.g., based on the transport signal value VTS), the controller 186 would automatically "stop" operation of the lift mechanism 108 (e.g., to stop powering the actuator 188), and would operate the indicator 220 in the first state 220A as noted above. However, certain aspects of the patient transport apparatus 100 may be configured without an automatic input control 218C, such that the user U would have to utilize the first and second input controls 218A, 218B to adjust the litter 106 between the lift configurations LC via the actuator 188. Furthermore, it is possible that the user U may prefer not to utilize the automatic input control 218C, even if available, or might otherwise rely on the first and second input controls 218A, 218B out of preference, habit, and the like. Nevertheless, the functionality afforded by the controller 186 and the user interface 216 introduced above help ensure that the user U can place the litter 106 in the transport configuration LCT in a reliable, simple, and repeatable manner as described in greater detail below.

In FIG. 7A, which represents a use scenario where the litter 106 is arranged in the fully-retracted configuration LCR as noted above, the user U has decided to move toward the transport configuration LCT using the first input control 218A. Here, the indicator 220 is shown operating in the second state 220B to communicate to the user U that the litter 106 is arranged in one of the plurality of lift configurations LC other than the transport configuration LCT, based on the signal SH generated by the height sensor 238A differing from the transport signal value VTS. This illustrative use scenario is represented in FIG. 6A by indicia S1A.

Figure 7B:
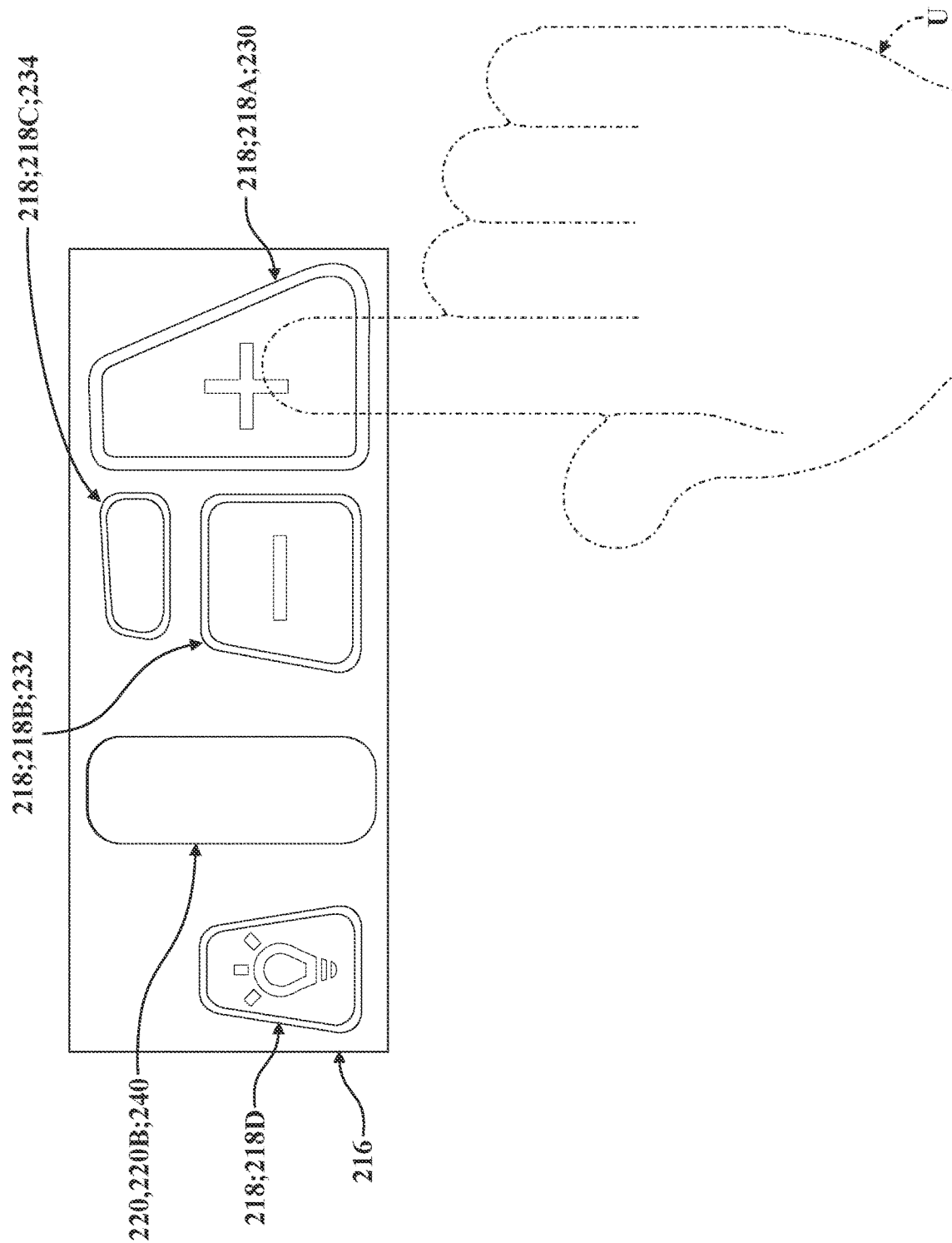
FIG. 7B is another schematic view of the user interface of FIG. 7A, shown with a user engaging a first input control to move the litter toward a fully-extended configuration, and with the indicator operating in one state to communicate to the user that the litter is arranged in a lift configuration other than a transport configuration.

Continuing from FIG. 7A to FIG. 7B, the user U is shown engaging the first input control 218A to "raise" the litter 106 toward the transport configuration LCT via the lift mechanism 108, and the litter 106 has moved closer toward the transport configuration LCT. This illustrative use scenario is represented in FIG. 6A by indicia S1B. Here, the indicator 220 remains in the second state 220B because the signal SH generated by the height sensor 238A still differs from the transport signal value VTS.

Figure 7C:
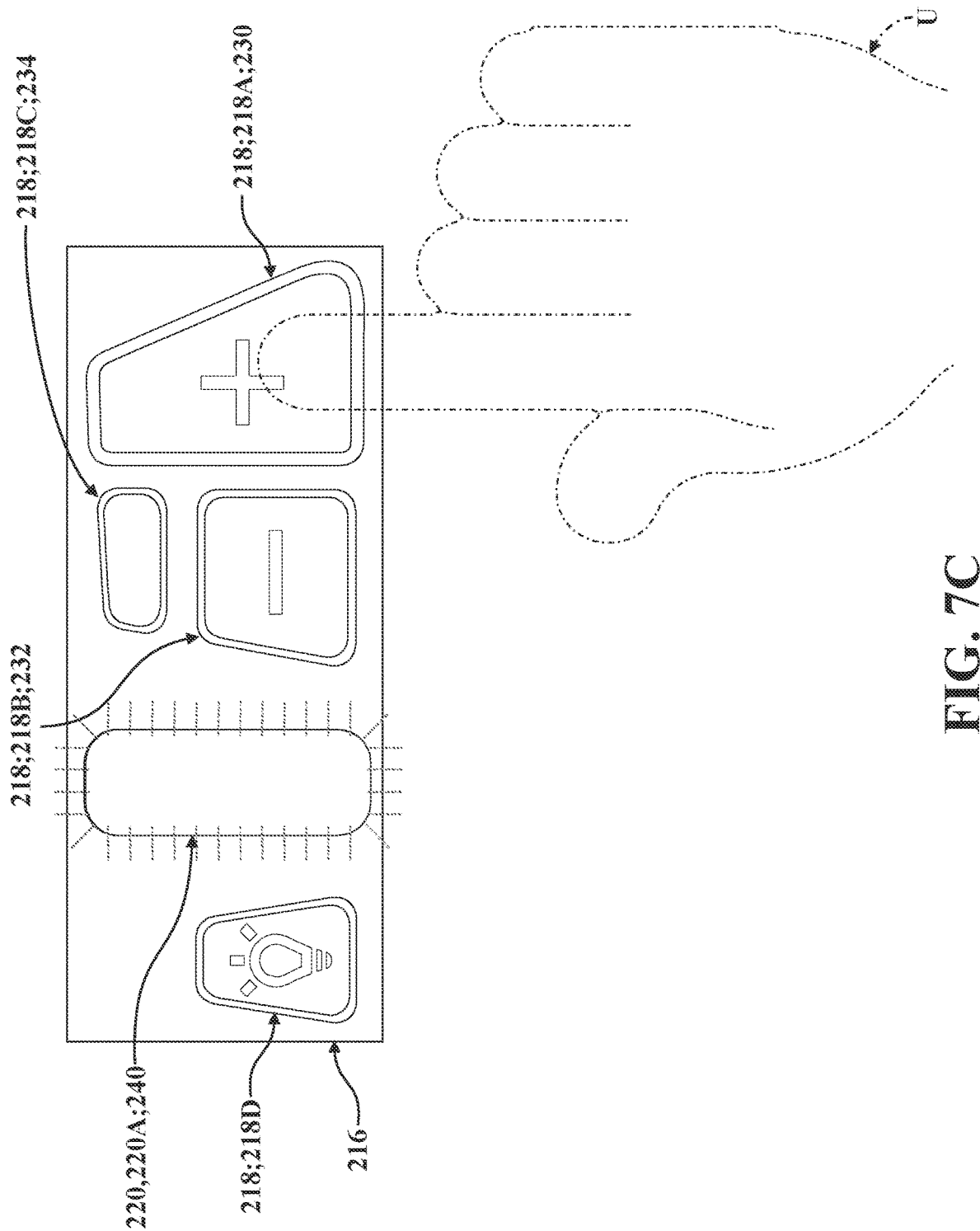
FIG. 7C is another schematic view of the user interface of FIGS. 7A-7B, shown with the user still engaging the first input control, and with the indicator operating in another state to communicate to the user that the litter is arranged in a transport configuration.

Continuing from FIG. 7B to FIG. 7C, the user U is shown still engaging the first input control 218A to "raise" the litter 106 via the lift mechanism 108, and the litter 106 has just reached the transport configuration LCT. This illustrative use scenario is represented in FIG. 6A by indicia S1C. Here, the indicator 220 has changed to the first state 220A because the signal SH generated by the height sensor 238A corresponds the transport signal value VTS. While this change is communicated via the indicator 220, in the illustrative use scenario depicted in FIG. 7C, the user U continues to engage the first input control 218A. Here, the user U could have their attention focused elsewhere and may not immediately see that the indicator 220 is now operating in the first state 220A.

Figure 7D:
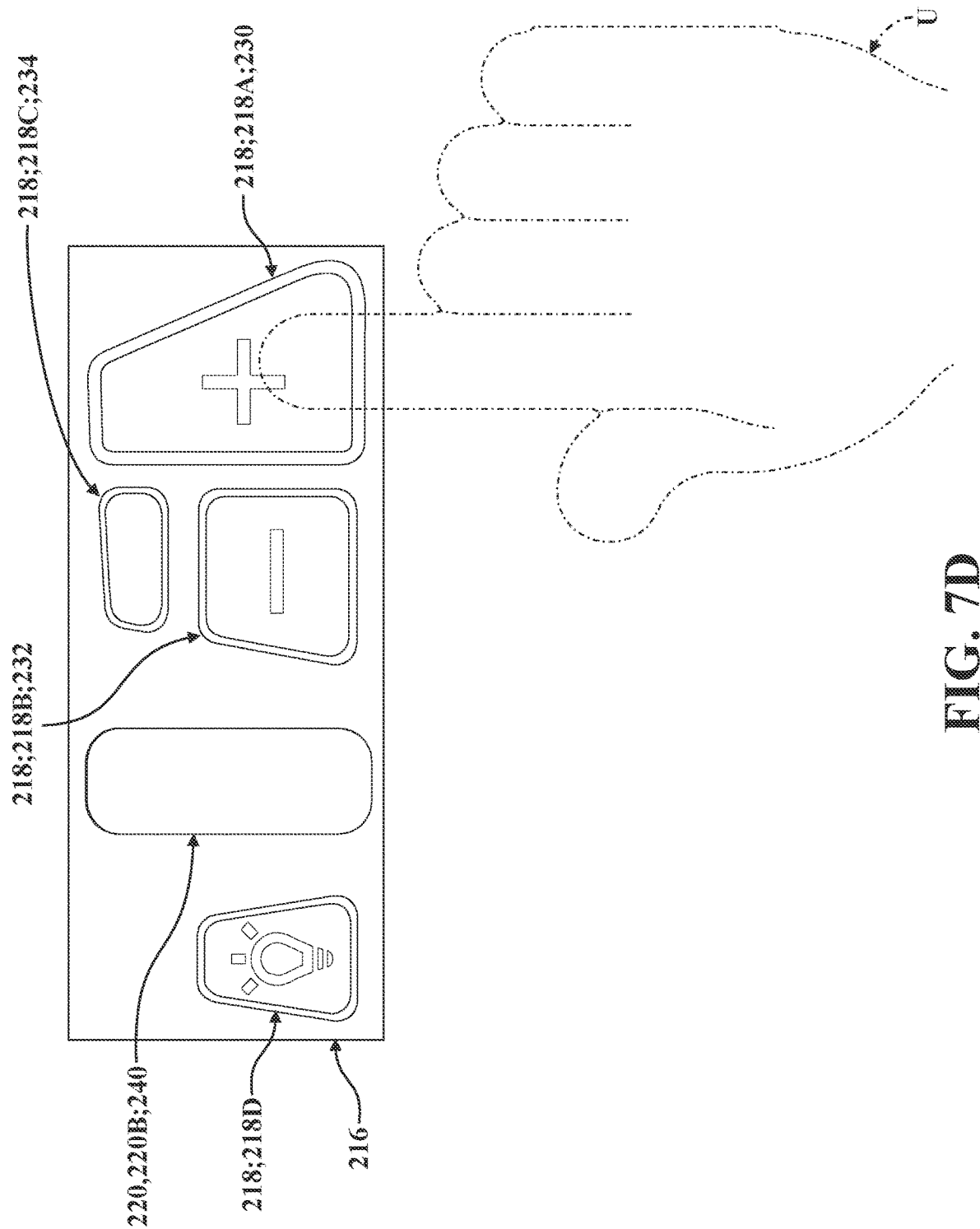
FIG. 7D is another schematic view of the user interface of FIGS. 7A-7C, shown with the user still engaging the first input control, and with the indicator operating in the state to communicate to the user that the litter is arranged in a lift configuration other than the transport configuration.

Continuing from FIG. 7C to FIG. 7D, the user U is shown still engaging the first input control 218A to "raise" the litter 106 via the lift mechanism 108, and the litter 106 has just passed transport configuration LCT and is moving toward the fully-extended configuration LCE. This illustrative use scenario is represented in FIG. 6A by indicia S1D. Here, the indicator 220 has changed back to the second state 220B because the signal SH generated by the height sensor 238A no longer corresponds the transport signal value VTS. In this illustrative use scenario, the user U only just noticed the change in state of the indicator 220 but has not yet disengaged the first input control 218A.

Figure 7E:
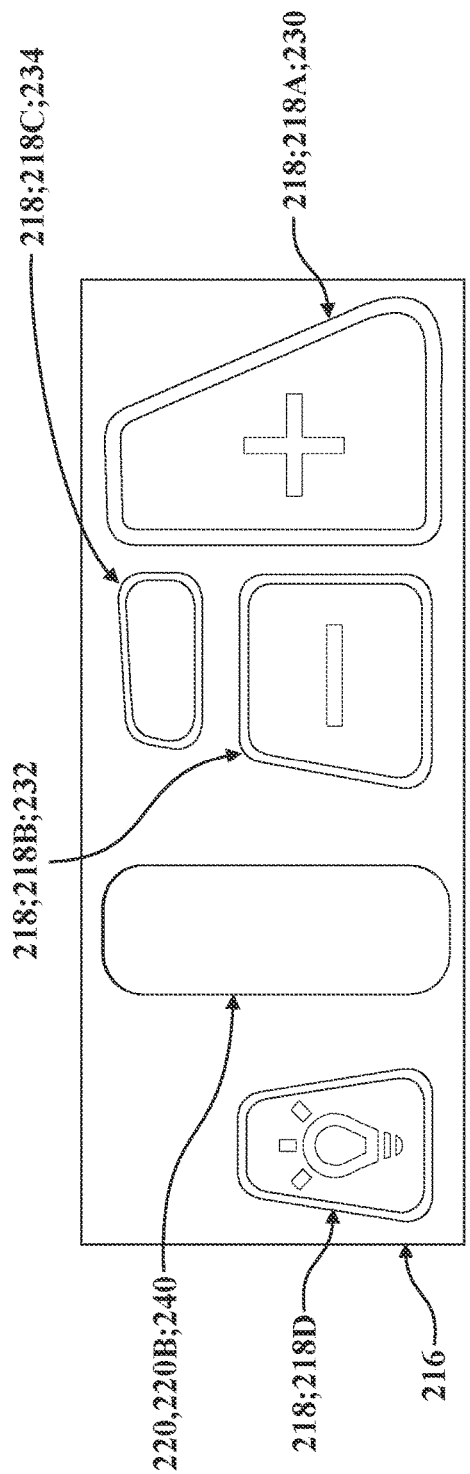
FIG. 7E is another schematic view of the user interface of FIGS. 7A-7D, shown with the user having disengaged the first input control, and with the indicator still operating in the state to communicate to the user that the litter is arranged in a lift configuration other than the transport configuration.

Continuing from FIG. 7D to FIG. 7E, the user U has disengaged the first input control 218A after having noticed the change in state of the indicator 220 from the first state 220A to the second state 220B. This illustrative use scenario is represented in FIG. 6A by indicia S1E. Here in this illustrative use scenario, the user U disengaged the first input control 218A where the litter 106 was positioned "just above" the transport configuration LCT, with the signal SH generated by the height sensor 238A being within the predetermined threshold VTH of the transport signal value VTS (see FIG. 6A).

Figure 7F:
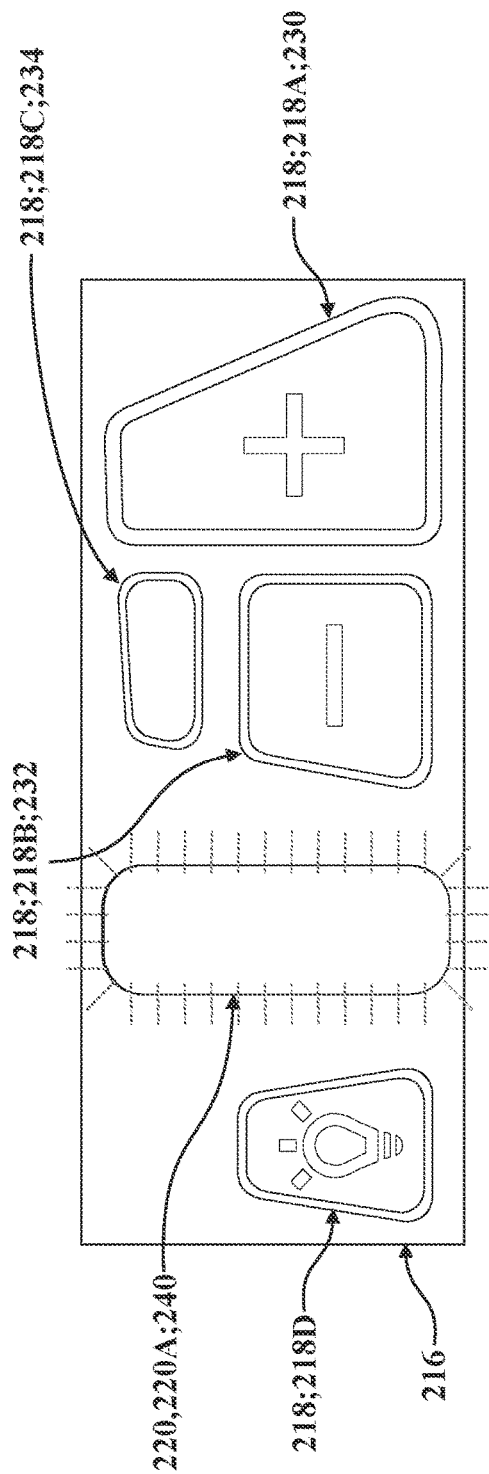
FIG. 7F is another schematic view of the user interface of FIGS. 7A-7E, shown with the user remaining disengaged from the first input control, and with the indicator now operating in the state to communicate to the user that the litter is arranged in the transport configuration based on automatic movement of the lift mechanism back toward the transport configuration effected via a controller of the control system.

Continuing from FIG. 7E to FIG. 7F, the user U remains disengaged from the first input control 218A, but the controller 186 has automatically driven the actuator 188 of the lift mechanism 108 to "lower" the litter 106 back toward and into the transport configuration LCT because the user U disengaged the first input control 218A while the signal SH generated by the height sensor 238A was within the predetermined threshold VTH of the transport signal value VTS. This illustrative use scenario is represented in FIG. 6A by indicia S1F. Here in FIG. 7F, the indicator 220 has changed back to the first state 220A because the signal SH generated by the height sensor 238A again corresponds the transport signal value VTS.

The forgoing example illustrates one way that the controller 186 can "automatically correct" the litter 106 toward the transport configuration LCT based on disengagement of the input controls 218 which suggests or otherwise indicates that the user U does desire to place the litter 106 in the transport configuration LCT. It will be appreciated that the predetermined threshold VTH can be adjusted in different ways to suit different applications, users U, and the like, as well as for different types of patient transport apparatuses 100. In some aspects, the predetermined threshold VTH could be a relatively small value such that the user U would have to disengage the input controls 218 relatively "quickly" after passing the transport configuration LCT. In some aspects, the predetermined threshold VTH could be a larger value such that the user U could have more time to disengage the input controls 218 after passing the transport configuration LCT while still ensuring that the "automatic correction" of the litter 106 would function. In some aspects, another input control 218 (e.g., a separate switch or button) could be used to "override" or "disable" this functionality either temporarily or based on user U preferences/policy. In some aspects, the predetermined threshold VTH could be adjustable, such as by the user U and/or by a service technician. In some aspects, different predetermined thresholds VTH could be utilized depending on whether the user U was "extending" or "retracting" the lift mechanism 108. Other configurations are contemplated.

As noted above, the controller 186 is configured to operate the indicator 220 in the first state 220A when the signal SH generated by the height sensor 238A corresponds to the transport signal value VTS to communicate to the user U that the litter 106 is arranged in the transport configuration LCT, and to operate the indicator 220 in the second state 220B when the signal SH generated by the height sensor 238A differs from the transport signal value VTS to communicate to the user U that the litter 106 is arranged in one of the plurality of lift configurations LC other than the transport configuration LCT. In some aspects, however, the indicator 220 may be further operable in a third state 220C different from both the first state 220A and the second state 220B. In such aspects, both the second state 220B and the third state 220C are configured to communicate to the user U that the litter 106 is arranged in one of the plurality of lift configurations LC other than the transport configuration LCT, but are different from each other to communicate additional information to the user U about the litter 106.

To this end, and according to aspects such as those described in greater detail below in connection with FIGS. 8A-8F, the controller 186 may be further configured to operate the indicator 220 in the second state 220B when the signal SH generated by the height sensor 238A indicates that the litter 106 is disposed in one of the plurality of lift configurations LC between the fully-retracted configuration LCR and the transport configuration LCT to communicate to the user U that the litter 106 is below the transport configuration LCT, and to operate the indicator 220 in the third state 220C when the signal SH generated by the height sensor 238A indicates that the litter 106 is disposed in one of the plurality of lift configurations LC between the transport configuration LCT and the fully-retracted configuration LCR to communicate to the user U that the litter 106 is above the transport configuration LCT. Thus, in some aspects, the indicator 220 can be used to communicate to the user U whether the litter 106 is at, above, or below the transport configuration LCT. This concept is illustrated by successively comparing FIGS. 8A-8F with reference to FIG. 6B.

In the representative aspects illustrated in FIGS. 8A-8F, the indicator 220 similarly comprises the light source 240, such as one or more single or multi-color light-emitting diodes (LEDs). However, in this aspect, the first state 220A of the indicator 220 is further defined as light emission via the light source 240 at a first wavelength W1 (e.g., blue visible light), the second state 220B of the indicator 220 is further defined as light emission via the light source 240 at a second wavelength W2 (e.g., purple visible light) different from the first wavelength W1, and the third state 220C of the indicator 220 is further defined as light emission via the light source 240 at a third wavelength W3 (e.g., orange visible light) different from the first wavelength W1 and from the second wavelength W2. However, it will be appreciated that other configurations are contemplated, and one of the first, second, and third states 220A, 220B, 220C could be defined by an absence of light emission in some aspects.

Figure 6B:
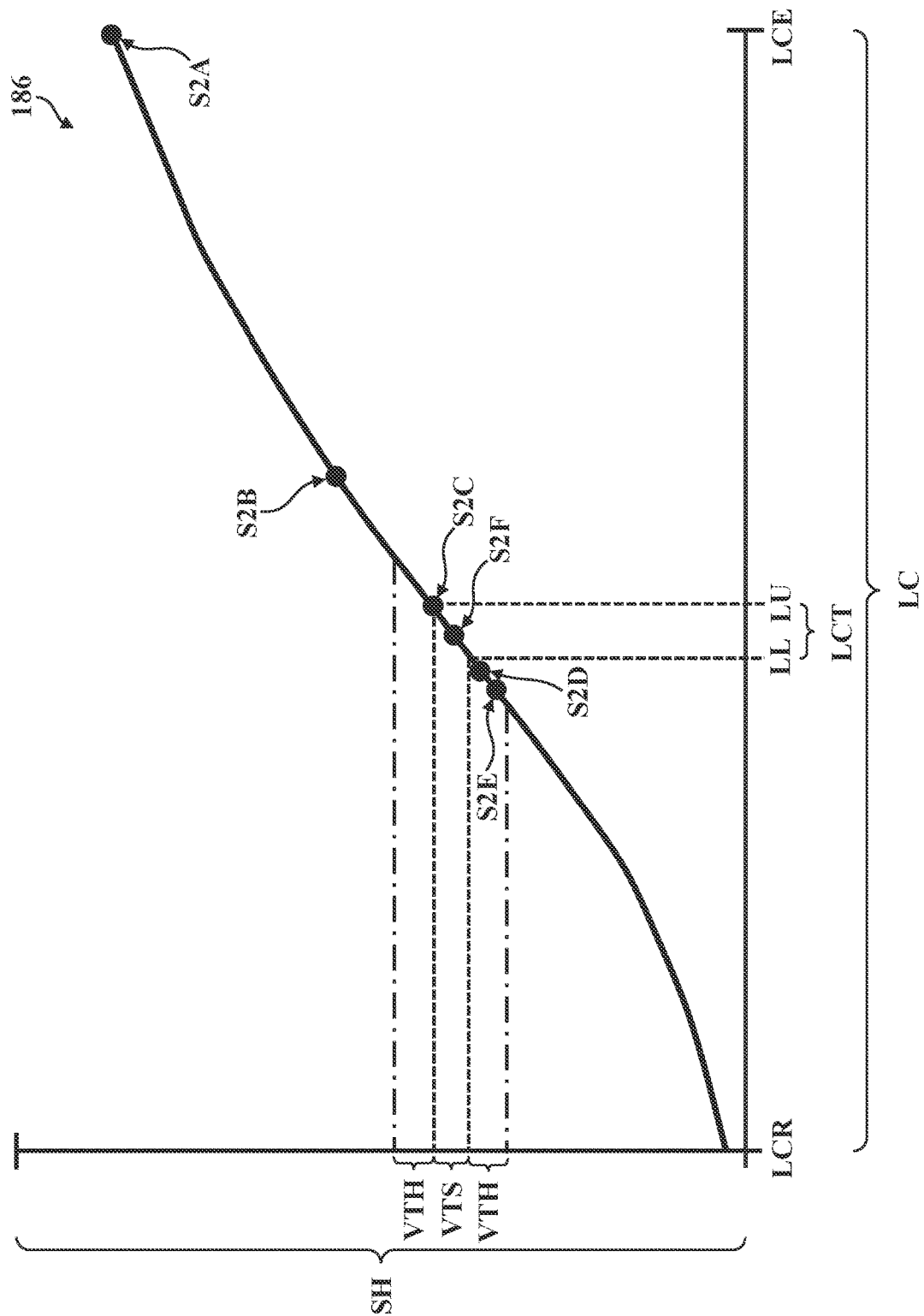
FIG. 6B is another graphical representation of various lift configurations of the patient transport apparatus of FIG. 1 plotted against height sensor signal data to illustrate transport configurations between the fully-retracted configuration and the fully-extended configuration.
Figure 8A:
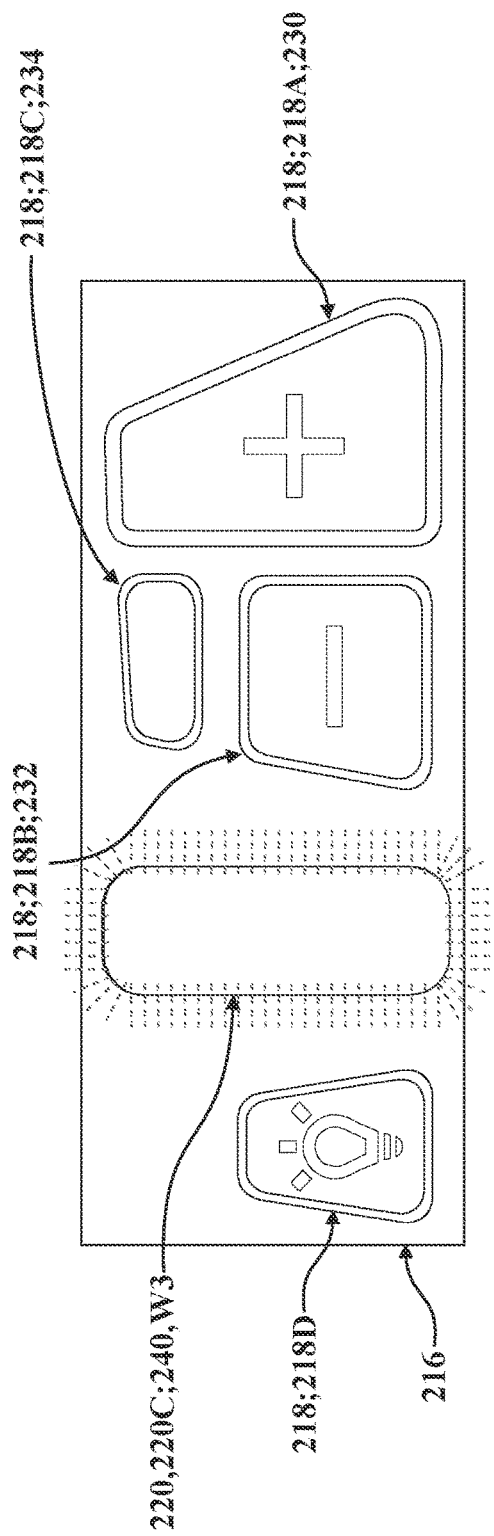
FIG. 8A is a schematic view of a user interface of the patient transport apparatus of FIGS. 1-7F, shown having input controls and an indicator according to aspects of the present disclosure, and shown with the indicator operating in one state to communicate to the user that the litter is arranged in a lift configuration higher than a transport configuration.

For illustrative purposes, FIG. 8A may represent a use scenario where the user U is about to utilize the user interface 216 to "lower" the patient transport apparatus 100 from the fully-extended configuration LCR depicted in FIG. 3A, and desires to place the litter 106 in the transport configuration LCT depicted in FIG. 3C. In this exemplary use scenario, the user U has decided to move toward the transport configuration LCT using the second input control 218B. Here, the indicator 220 is shown operating in the third state 220C to communicate to the user U that the litter 106 is above the transport configuration LCT based on the signal SH generated by the height sensor 238A. This illustrative use scenario is represented in FIG. 6B by indicia S2A.

Figure 8B:
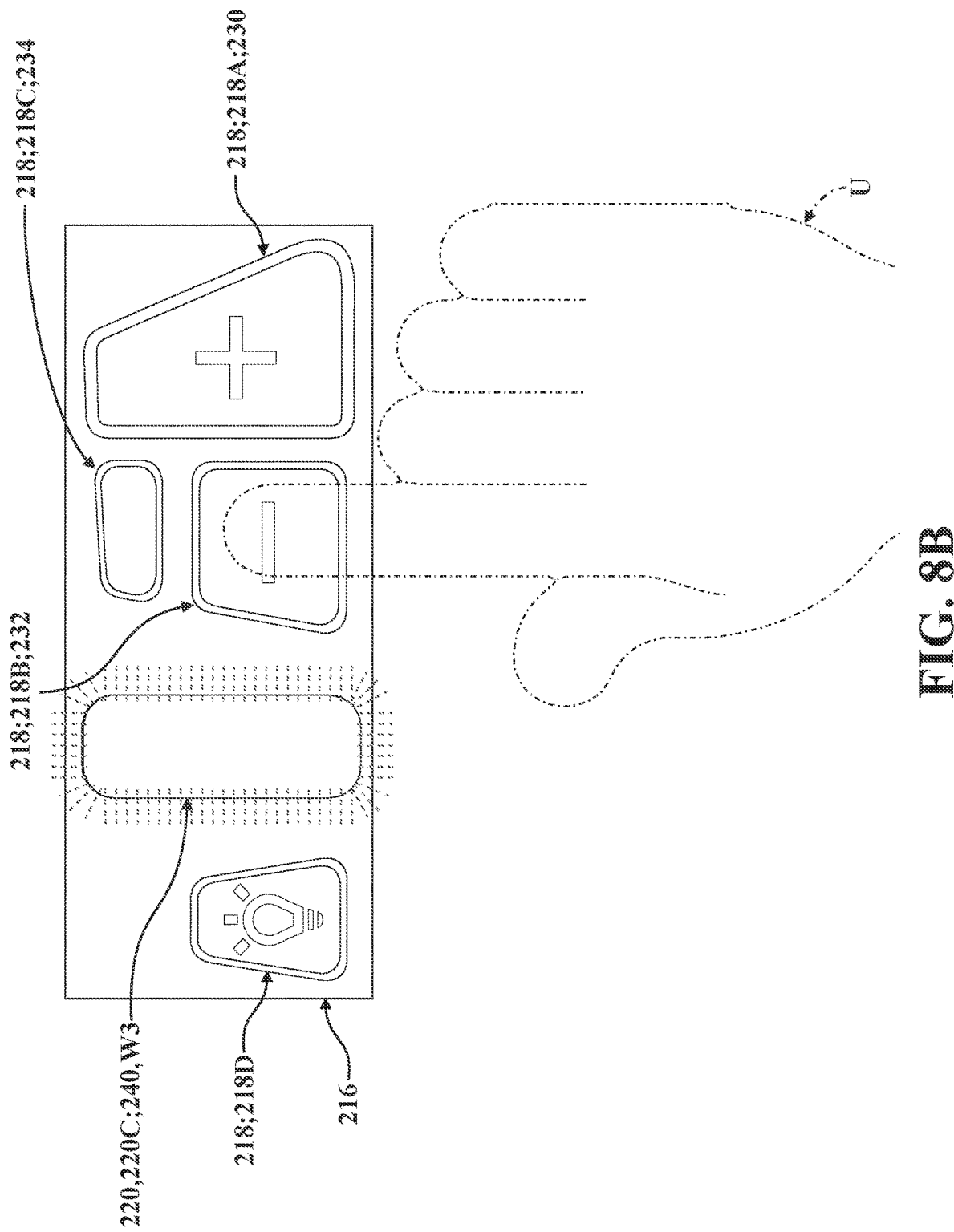
FIG. 8B is another schematic view of the user interface of FIG. 8A, shown with a user engaging a second input control to move the litter toward a fully-retracted configuration, and with the indicator operating in the state to communicate to the user that the litter is arranged in a lift configuration higher than a transport configuration.

Continuing from FIG. 8A to FIG. 8B, the user U is shown engaging the second input control 218B to "lower" the litter 106 toward the transport configuration LCT via the lift mechanism 108, and the litter 106 has moved closer toward the transport configuration LCT. This illustrative use scenario is represented in FIG. 6B by indicia S2B. Here, the indicator 220 remains in the third state 220C because the signal SH generated by the height sensor 238A still differs from the transport signal value VTS and still indicates that the litter 106 is "higher" than the transport configuration LCT.

Continuing from FIG. 8B to FIG. 8C, the user U is shown still engaging the second input control 218B to "lower" the litter 106 via the lift mechanism 108, and the litter 106 has just reached the transport configuration LCT. This illustrative use scenario is represented in FIG. 6B by indicia S2C. Here, the indicator 220 has changed to the first state 220A because the signal SH generated by the height sensor 238A corresponds the transport signal value VTS. While this change is communicated via the indicator 220, in the illustrative use scenario depicted in FIG. 8C, the user U continues to engage the second input control 218B. Here, the user U could have their attention focused elsewhere and may not immediately see that the indicator 220 is now operating in the first state 220A.

Continuing from FIG. 8C to FIG. 8D, the user U is shown still engaging the second input control 218B to "lower" the litter 106 via the lift mechanism 108, and the litter 106 has just passed transport configuration LCT and is moving toward the fully-retracted configuration LCR. This illustrative use scenario is represented in FIG. 6B by indicia S2D. Here, the indicator 220 has now changed to the second state 220B to communicate to the user U that the litter 106 is below the transport configuration LCT based on the signal SH generated by the height sensor 238A. In this illustrative use scenario, the user U only just noticed the change in state of the indicator 220 but has not yet disengaged the second input control 218B.

Figure 8E:
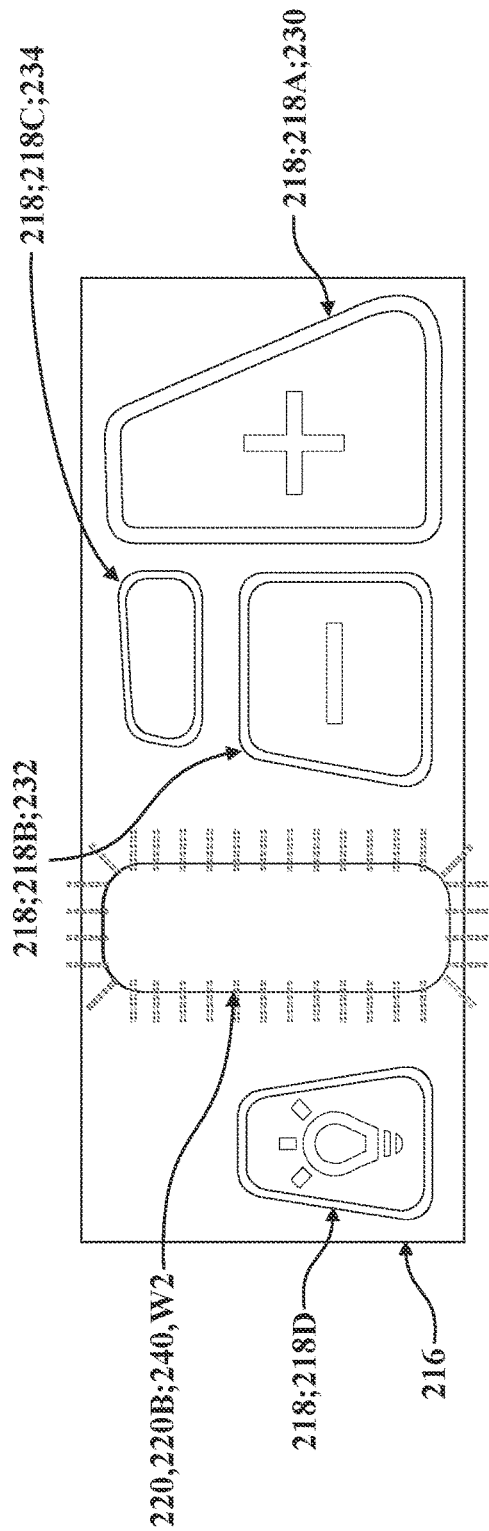
FIG. 8E is another schematic view of the user interface of FIGS. 8A-8D, shown with the user having disengaged the second input control, and with the indicator still operating in the state to communicate to the user that the litter is arranged in a lift configuration lower than the transport configuration.

Continuing from FIG. 8D to FIG. 8E, the user U has disengaged the second input control 218B after having noticed the change in state of the indicator 220 from the first state 220A to the second state 220B. This illustrative use scenario is represented in FIG. 6B by indicia S2E. Here in this illustrative use scenario, the user U disengaged the second input control 218B where the litter 106 was positioned "just below" the transport configuration LCT, with the signal SH generated by the height sensor 238A being within the predetermined threshold VTH of the transport signal value VTS (see FIG. 6B).

Figure 8F:
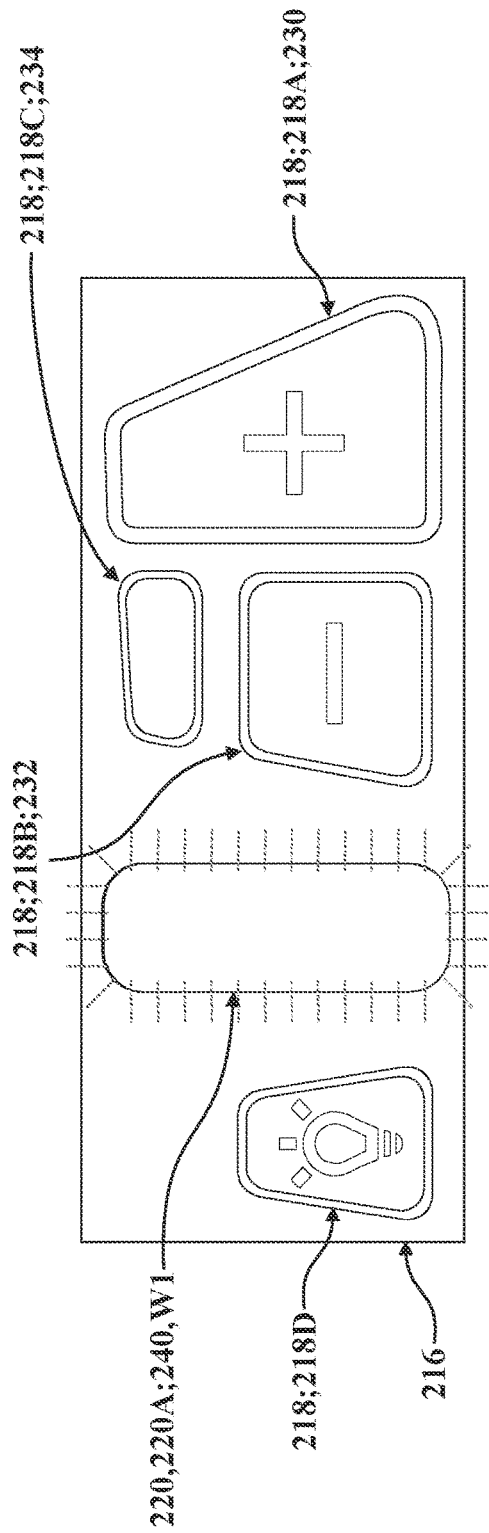
FIG. 8F is another schematic view of the user interface of FIGS. 8A-8E, shown with the user remaining disengaged from the second input control, and with the indicator now operating in the state to communicate to the user that the litter is arranged in the transport configuration based on automatic movement of the lift mechanism back toward the transport configuration effected via the controller of the control system.

Continuing from FIG. 8E to FIG. 8F, the user U remains disengaged from the second input control 218B, but the controller 186 has automatically driven the actuator 188 of the lift mechanism 108 to "raise" the litter 106 back toward and into the transport configuration LCT because the user U disengaged the second input control 218B while the signal SH generated by the height sensor 238A was within the predetermined threshold VTH of the transport signal value VTS. This illustrative use scenario is represented in FIG. 6B by indicia S2F. Here in FIG. 8F, the indicator 220 has changed back to the first state 220A because the signal SH generated by the height sensor 238A again corresponds the transport signal value VTS.

Referring now to FIG. 2, as noted above, the user interface 216 of the patient transport apparatus 100 may comprise input controls 218 and/or indicators 220 of various styles, types, configurations, and arrangements. In some aspects, indicators 220 realized as light sources 240 may be utilized, as noted above. In some aspects, indicators 220 realized as audible generators 242 may be employed, where the first state 220A could be defined by a short "beep" or another noise, sound, and the like to communicate to the user U that the litter 106 is in or has reached the transport configuration LCT. In some aspects, indicators 220 realized as haptic generators 244 may be employed, where the first state 220A could be defined by a haptic pulse, a vibration, a "buzz" or "click" feeling generated by a motor, a piezoelectric device, and the like arranged adjacent to the user interface 216 to communicate to the user U that the litter 106 is in or has reached the transport configuration LCT. Other configurations are contemplated.

Referring now to FIGS. 2-3C, in some aspects, an auxiliary user interface 246 operatively connected to the controller 186 (e.g., via wireless electrical communication) may be employed. In the representative aspect illustrated herein, the auxiliary user interface 246 comprises an auxiliary indicator 248 operable between a first auxiliary state 248A and a second auxiliary state 248B different from the first auxiliary state 248A. Here, the controller 186 is further configured to operate the auxiliary indicator 248 in the first auxiliary state 248A when the signal SH generated by the height sensor 238A corresponds to the transport signal value VTS to communicate to the user U that the litter 106 is arranged in the transport configuration LCT, and to operate the auxiliary indicator 248 in the second auxiliary state 248B when the signal SH generated by the height sensor 238A differs from the transport signal value VTS to communicate to the user U that the litter 106 is arranged in one of the plurality of lift configurations LC other than the transport configuration LCT.

In some aspects, the auxiliary user interface 246 may form part of the patient transport apparatus 100, realized such as by a tethered pendant, remote control, and the like. In some aspects, the auxiliary user interface 246 may comprise a haptic generator 244, and the first auxiliary state 248A of the auxiliary indicator 248 may be further defined as a haptic pulse generated by the haptic generator 244. Other configurations are contemplated. In the representative aspect illustrated herein, the auxiliary user interface 246 is not realized as a part of the patient transport apparatus 100. Rather, and as is depicted in FIGS. 2-3C, the auxiliary user interface 246 may form part of a portable electronic device 250 (e.g., a cellular or mobile phone) that is carried by the user U, and/or a wearable electronic device 252 (e.g., a "smartwatch"), that is disposed in wireless electrical communication with the controller 186 such as via one or transmitters and/or receivers that communicate using one or more protocols (e.g., Bluetooth®, Wi-Fi, Near-Field Communication, Radio-frequency Identification, and the like). Other configurations are contemplated. Here for example, if the user U were outfitted as depicted in FIGS. 3A-3C with a portable electronic device 250 disposed in their pocket, and/or with a wearable electronic device 252 coupled to their wrist, serving as an auxiliary user interface 246 with a haptic generator 244 and with suitable software installed thereon (e.g., an application or program), the controller 186 could transmit signals to the portable and/or wearable electronic device 252 to activate the haptic generator 244 in the first auxiliary state 248A when movement of the lift mechanism 108 brings the litter 106 into the transport configuration LCT. Here, it will be appreciated that the user U can be alerted when the litter 106 is disposed in the transport configuration LCT without requiring that their attention be focused on the light source 240. However, other configurations are contemplated, and it will be appreciated that various types of portable electronic device 250 and/or wearable electronic devices 252 may be utilized in some aspects, with auxiliary user interfaces 246 of various types, styles, and configurations (e.g., with input controls, different types of indicators, and the like).

In some aspects, the patient transport apparatus 100 may further comprise a load sensor 238B operatively connected to the controller 186 and configured to sense load, force, and the like acting on the base 104 and/or acting between the base 104 and the litter 106, and may generate a load signal SL corresponding to the load. Here, it will be appreciated that one or more load sensors 238B could be utilized, and could be configured to detect the presence of and/or measure the mass of an object that is supported on the litter 106 (e.g., the patient). For example, the load sensor 238B may detect that a patient has been placed on the patient support surface 122.

The load sensor 238B may form a part of or otherwise be utilized by the lift mechanism 108 to effect control of the actuator 188. In the aspect depicted in FIG. 4, for example, the load sensor 238B comprises a strain gauge operatively attached to the upper support 192. As such, the load sensor 238B may sense, via the strain gauge, force acting on the base 104 relative to the litter 106 based on a load applied to the actuator 188. Additionally, it will be appreciated that the strain gauge may be coupled to any component of the lift mechanism 108 suitable for sensing force acting on the base 104 relative to the litter 106, and/or for sensing force acting on the litter 106 relative to the base 104. For example, the load sensor 238B could be realized as a part of the actuator 188 (e.g., coupled to the reciprocal rod 198). Other configurations are contemplated. In some aspects, the load sensor 238B may comprise a load cell coupled to the lift mechanism 108 and being configured to sense a load applied to the lift mechanism 108, the load corresponding to the force being applied on the base 104 and/or load being applied on the litter 106. In some aspects, such as where the patient transport apparatus 100 utilizes a hydraulically-powered actuator 188 to move the litter 106 between the lift configurations LC, the load sensor 238B may comprise pressure switches, pressure transducers, and the like be disposed in fluid communication with the hydraulic actuator and may sense a pressure within the hydraulic actuator corresponding to the force acting on the base 104 (e.g., via force, weight, and the like applied to the litter 106). In some aspects, the load sensor 238B may include a current sensor configured to sense an electrical current drawn by the lift mechanism 108 corresponding to the force acting on the base 104. In some aspects, the load sensor 238B may include an accelerometer configured to sense a speed of a component of the patient transport apparatus 20 corresponding to the force acting on the base 104. Other configurations are contemplated.

Figure 6C:
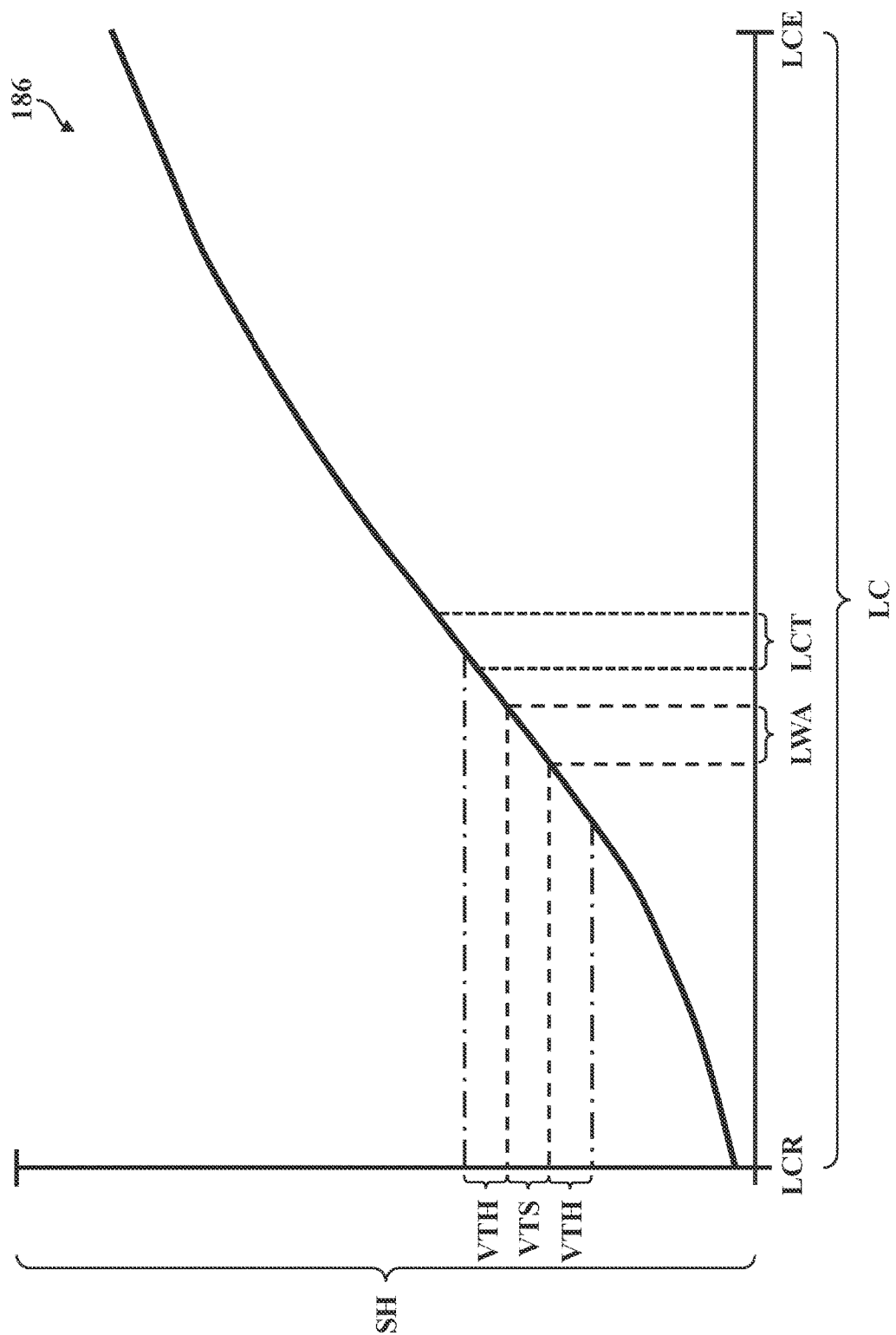
FIG. 6C is another graphical representation of the various lift configurations plotted against the height sensor signal data of FIGS. 6A-6B to illustrate weight-adjusted transport configurations.

Referring now to FIGS. 2 and 6C, in some aspects, the patient transport apparatus 100 may comprise a patient sensor 238C operatively connected to the controller 186 and configured to generate a patient signal SP associated with a weight of the patient supported by the litter 106. To this end, in some aspects, the patient sensor 238C may comprise the load sensor 238B described above. However, other configurations are contemplated. Here, and as is illustrated by the graph depicted in FIG. 6C, the controller 186 may be further configured to compare the patient signal SP generated by the patient sensor 238C against a weight safety threshold VWS to define a weight-adjusted transport configuration LWA to position the litter 106 at least partially lower than the transport configuration LCT, adjust the transport signal value VTS and the predetermined threshold VTH based on the weight-adjusted transport configuration LWA, and drive the lift mechanism 108 (e.g., via the actuator 188) to the weight-adjusted transport configuration LWA in response to the patient signal SP exceeding the weight safety threshold VWS and in response to the signal SH generated by the height sensor 238A being within a predetermined threshold (e.g., the predetermined threshold VTH described above, or another threshold) of the transport signal value VTS upon user U disengagement of the input control 218 of the user interface 216. Put differently, in this scenario, and as is depicted in FIG. 6C, the weight-adjusted transport configuration LWA would be used to define the transport signal value VTS and the predetermined threshold VTH (as opposed to the non-adjusted transport configuration LCT).

By utilizing the patient sensor 238C as described above, the controller 186 can help ensure that patients of different weights are transported with the litter 106 set to an appropriate height. Put differently, the transport configuration LCT can be adjusted so as to arrange the litter 106 closer to the base 104 when a relatively heavy patient is being transported compared to when a relatively lightweight patient is being transported. While the user U can select between a number of different lift configurations LC to transport the patient, use of the patient sensor 238C may advantageously automatically adjust away from what would otherwise be considered the "normal" transport configuration when a heavy patient is transported by, among other things, operating the indicator 220 in the first state 220A differently (e.g., with the litter 106 lower than it would otherwise be when operating in the first state 220A) when a relatively heavy patient is supported on the litter 106.

In some aspects, the indicator 220 may further be operable in a warning state 220D (not shown in detail) different from the first, second, and/or third states 220A, 220B, 220C. Here, for example, if the indicator 220 comprises the light source 240 as noted above, the warning state 220D may be realized by the indicator 220 flashing, blinking, or otherwise emitting light in a pattern to draw the attention of the user U. Similarly, if the indicator 220 comprises the audible generator 242, the warning state 220D may comprise a beeping alarm or another sound. Other configurations are contemplated. Here, the controller 186 may be further configured to operate the indicator 220 in the warning state 220D in response to the patient signal SP generated by the patient sensor 238C exceeding the weight safety threshold VWS and in response to the signal SH generated by the height sensor 238A indicating that the litter 106 is arranged higher than the weight-adjusted transport configuration LWA. In this way, in scenarios where the user U is transporting the patient with the litter 106 arranged too high based on the weight of the patient, the indicator 220 can be used to alert the user U and/or prompt the user U to lower the litter 106. It is contemplated that additional sensors, such as a movement sensor 238D, could be used to ensure that the indicator 220 only operates in the warning state 220D occasionally (e.g., for a period of time following movement and during an absence of movement). In some aspects, the user interface 216 could be configured to permit the user U to disable or override operation in the warning state 220D. Other configurations are contemplated.

Figure 6D:
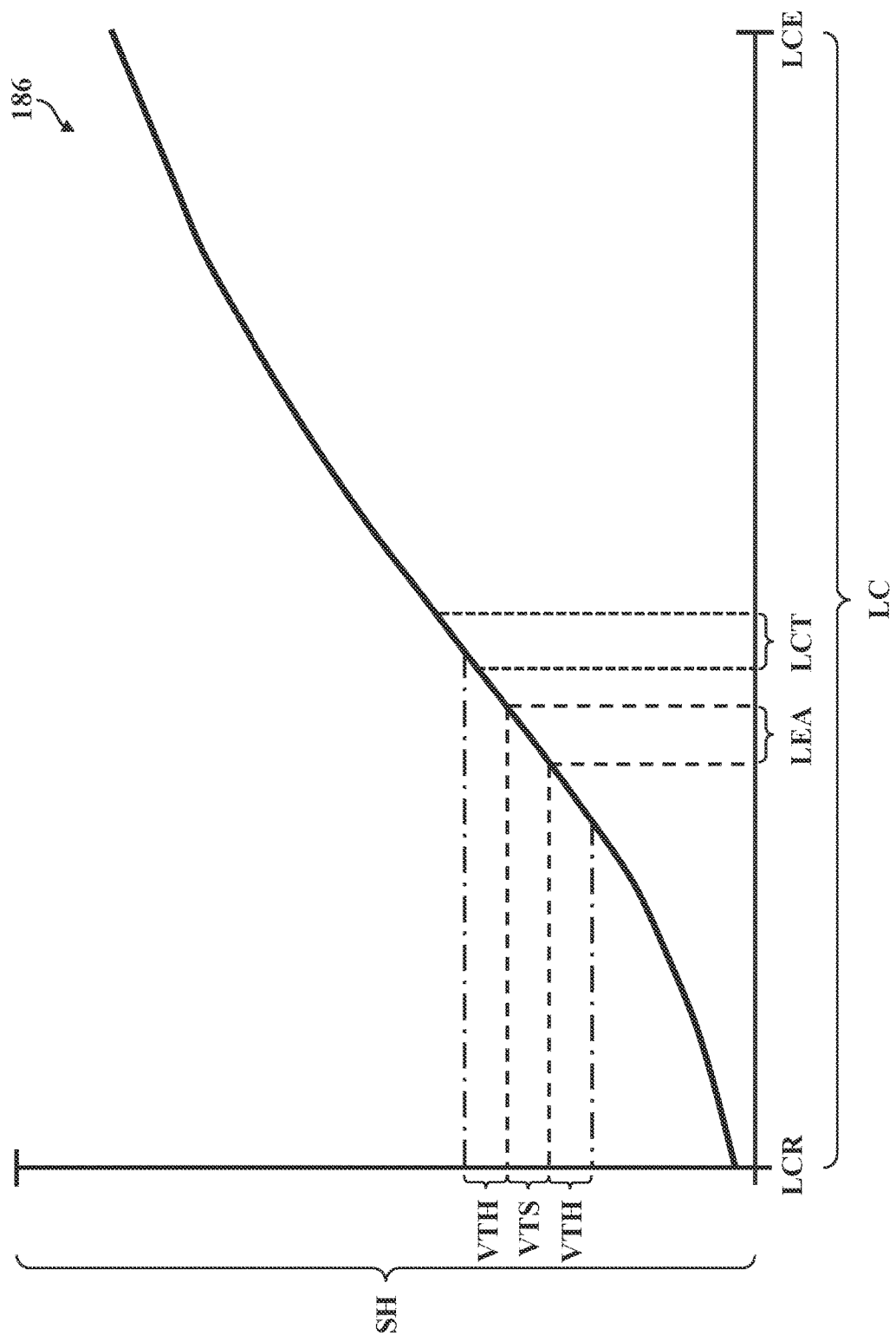
FIG. 6D is another graphical representation of the various lift configurations plotted against the height sensor signal data of FIGS. 6A-6B to illustrate environmentally-adjusted transport configurations.

Referring now to FIGS. 2 and 6D, in some aspects, the patient transport apparatus 100 may comprise an environmental sensor 238E operatively connected to the controller 186 and configured to generate a environment signal SE associated with an environment adjacent to the patient transport apparatus 100. Here, for example, the environmental sensor 238E may be configured to determine the geographical location of the patient transport apparatus 100 (e.g., realized such as with a global positioning system GPS sensor). In some aspects, the environmental sensor 238E may be configured to determine a location of the patient transport apparatus 100 relative to a reference location. The reference location may be a vehicle (e.g., an ambulance) or a building (e.g., a hospital or medical facility). In some aspects, the environmental sensor 238E may be configured to determine orientation, position, velocity, and/or acceleration of the patient transport apparatus 100 (e.g., via accelerometers, gyroscopes, movement sensors, rotation sensors, and the like). In some aspects, the environmental sensor 238E may be configured to determine aspects of the terrain, weather, and the like (e.g., to detect slippery surfaces, stairs, inclines, hills, rough terrain, and the like). Other configurations are contemplated.

As is illustrated by the graph depicted in FIG. 6C, by using the environmental sensor 238D, the controller 186 may be further configured to compare the environment signal SE generated by the environmental sensor 238D against an environmental safety threshold VES to define a environmentally-adjusted transport configuration LEA to position the litter 106 at least partially lower than the transport configuration LCT, adjust the transport signal value VTS and the predetermined threshold VTH based on the environmentally-adjusted transport configuration LEA, and drive the lift mechanism 108 (e.g., via the actuator 188) to the environmentally-adjusted transport configuration LEA in response to the environment signal SE exceeding the environmental safety threshold VES and in response to the signal SH generated by the height sensor 238A being within a predetermined threshold (e.g., the predetermined threshold VTH described above, or another threshold) of the transport signal value VTS upon user U disengagement of the input control 218 of the user interface 216. Put differently, in this scenario, and as is depicted in FIG. 6D, the environmentally-adjusted transport configuration LEA would be used to define the transport signal value VTS and the predetermined threshold VTH (as opposed to the non-adjusted transport configuration LCT).

By utilizing the environmental sensor 238D as described above, the controller 186 can help ensure that patients are transported with the litter 106 set to an appropriate height based on environmental conditions. Put differently, the transport configuration LCT can be adjusted so as to arrange the litter 106 closer to the base 104 when there is a greater risk of tipping the patient transport apparatus 100, where handling or moving/maneuvering the patient transport apparatus 100 would ordinarily be more difficult for the user U, and the like. While the user U can select between a number of different lift configurations LC to transport the patient, use of the environmental sensor 238D may advantageously automatically adjust away from what would otherwise be considered the "normal" transport configuration when there are increased environmental risk factors.

In some aspects, the indicator 220 may further be operable in the warning state 220D as noted above (see FIG. 2). Here, the controller 186 may be further configured to operate the indicator 220 in the warning state 220D in response to the environment signal SE generated by the environmental sensor 238D exceeding the environmental safety threshold VES and in response to the signal SH generated by the height sensor 238A indicating that the litter 106 is arranged higher than the environmentally-adjusted transport configuration LEA. In this way, in scenarios where the user U is transporting the patient with the litter 106 arranged too high based on one or more environmental risk factors, the indicator 220 can be used to alert the user U and/or prompt the user U to lower the litter 106. Here too, it is contemplated that additional sensors, such the a movement sensor 238D, could be used to ensure that the indicator 220 only operates in the warning state 220D occasionally (e.g., for a period of time following movement and during an absence of movement). In some aspects, the user interface 216 could be configured to permit the user U to disable or override operation in the warning state 220D. Other configurations are contemplated.

Referring now to FIGS. 2-3C and 6E, in some aspects, the patient transport apparatus 100 may further comprise an identification sensor 238F to generate an identity signal SI associated with an identify of the user U. To this end, the identification sensor 238F may comprise a reader (e.g., a radio-frequency identification RFID reader) configured to scan or otherwise identity tokens 254 (e.g., radio-frequency identification RFID tags, badges, and the like) worn or otherwise carried by different users U. Here, by comparing the identity signal SI generated by the identification sensor 238F against a list of users 256 (see FIG. 2) stored in the memory 228, the controller 186 can determine the identity of the user U or otherwise differentiate between different known users U. For example, data stored in the memory 228 could be used to differentiate between different users U based on which token 254 is identified by the identification sensor 238F according to the identity signal SI. It will be appreciated that other types of identity sensors 238F could be used, of various types sufficient to differentiate between different users U, without departing from the scope of the present disclosure.

Figure 6E:
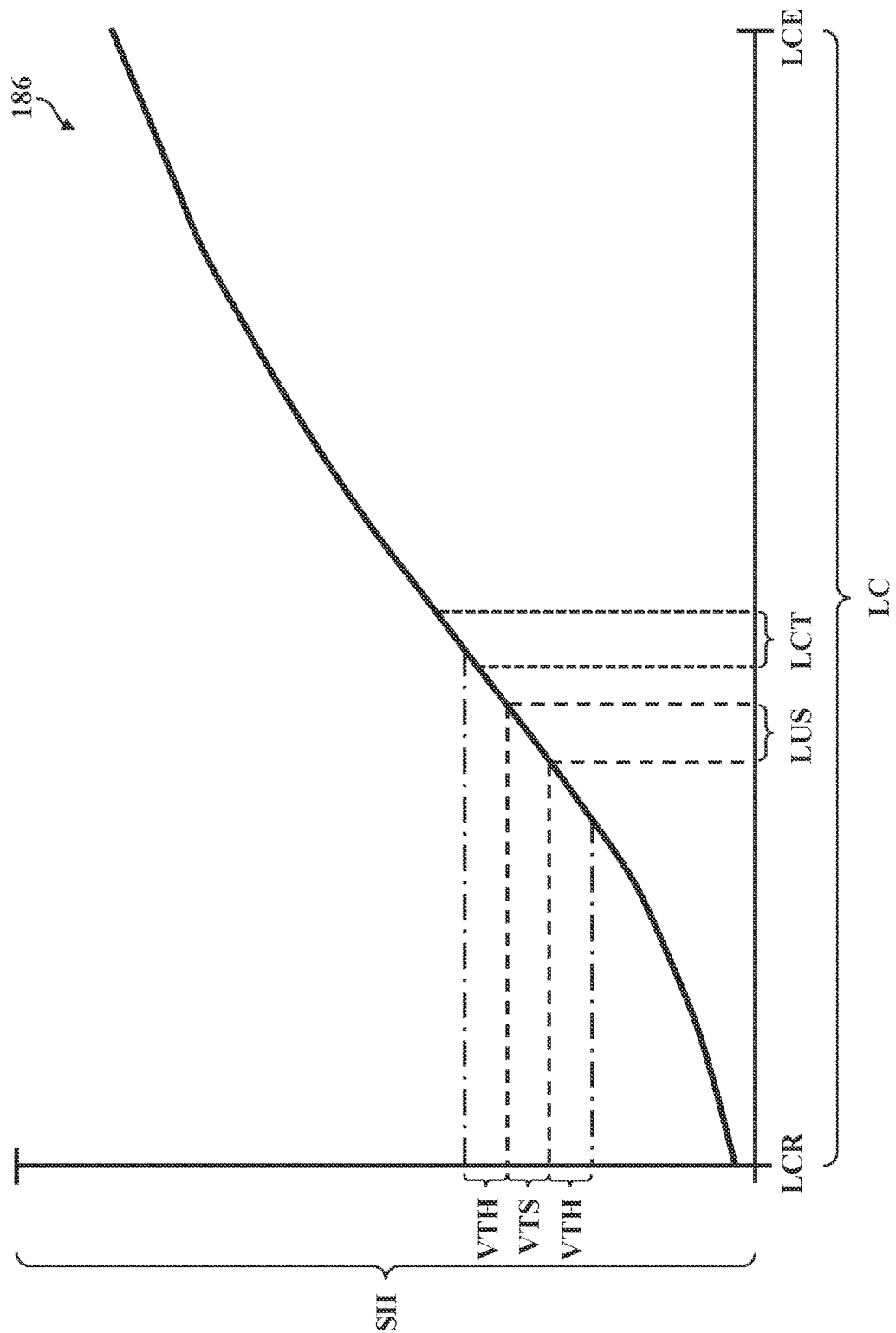
FIG. 6E is another graphical representation of the various lift configurations plotted against the height sensor signal data of FIGS. 6A-6B to illustrate user-specific transport configurations.

In some aspects, the controller 186 could be further configured to define a user-specific transport configuration LUS to position the litter 106 based on the identify of the user U determined based on the identity signal SI, adjust the transport signal value VTS and the predetermined threshold VTH based on the user-specific transport configuration LYS, and drive the lift mechanism 108 (e.g., via the actuator 188) to move to the user-specific transport configuration LUS in response to detection of the identity signal SI and in response to the signal SH generated by the height sensor 238A being within a predetermined threshold (e.g., the predetermined threshold VTH described above, or another threshold) of the transport signal value VTS upon user U disengagement of the input control 218 of the user interface 216. Put differently, in this scenario, and as is depicted in FIG. 6E, the user-specific transport configuration LUS would be used to define the transport signal value VTS and the predetermined threshold VTH (as opposed to the non-adjusted transport configuration LCT).

Accordingly, the patient transport apparatus 100 can be configured to automatically move to user-specific transport configurations LUS defined based on predetermined parameters associated with different users U when those users U each use the user interface 216. Here, for example, patient safety may be promoted by allowing a relatively tall user U to transport the patient supported on the litter 106 at a height that is higher than would be more appropriate for a different, relatively short user U. Put differently, the user-specific transport configuration LSU for a relatively short user U be closer to the fully-retracted configuration LCR than the user-specific transport configuration LSU for a relatively tall user U. It will be appreciated that the list of users 256 can be modified, updated, and the like in various ways (e.g., via a service tool, via the user interface 216, and the like). Other configurations are contemplated.

In this way, the aspects disclosed herein afford significant opportunities for transporting patients with patient transport apparatuses 100 in consistent, reliable ways while, at the same time, affording users U with improved usability and control of the lift mechanism 108.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient transport apparatus comprising:
a base;
a litter comprising a patient support surface to support a patient;
a lift mechanism to facilitate arranging the litter relative to the base between a plurality of lift configurations including a fully-retracted configuration, a fully-extended configuration, and a transport configuration between the fully-retracted configuration and the fully-extended configuration;
a user interface comprising an input control arranged for engagement by a user to operate the lift mechanism, and an indicator operable between a first state and a second state different from the first state;
a height sensor to generate a signal indicative of the arrangement of the patient support surface relative to the base between the plurality of lift configurations;
an environmental sensor to generate an environment signal indicative of an environment adjacent to the patient transport apparatus; and
a controller operably connected to the lift mechanism, the height sensor, the environmental sensor and the user interface, the controller comprising one or more processors and a non-transitory storage medium having stored thereon instructions that when executed by the one or more processors are configured to:
compare the signal generated by the height sensor against a transport signal value associated with the transport configuration,
operate the indicator in the first state when the signal generated by the height sensor corresponds to the transport signal value to communicate to the user that the litter is arranged in the transport configuration,
operate the indicator in the second state when the signal generated by the height sensor differs from the transport signal value to communicate to the user that the litter is arranged in one of the plurality of lift configurations other than the transport configuration, upon user engagement of the input control, drive the lift mechanism to move the litter relative to the base, during movement of the litter relative to the base and, in response to the signal generated by the height sensor being within a predetermined threshold of the transport signal value, automatically drive the lift mechanism to move the litter to the transport configuration upon user disengagement of the input control, compare the environment signal generated by the environmental sensor against an environmental safety threshold, define an environmentally-adjusted transport configuration to position the litter at least partially lower than the transport configuration, adjust the transport signal value and the predetermined threshold based on the environmentally-adjusted transport configuration, and drive the lift mechanism to move to the environmentally-adjusted transport configuration in response to the environment signal exceeding the environmental safety threshold and in response to the signal generated by the height sensor being within a predetermined threshold of the transport signal value upon user disengagement of the input control.

2. The patient transport apparatus of claim 1, wherein the transport configuration is defined by a plurality of lift configurations between the fully-retracted configuration and the fully-extended configuration.

3. The patient transport apparatus of claim 1, wherein the indicator comprises a light source.

4. The patient transport apparatus of claim 3, wherein the first state of the indicator is further defined as light emission via the light source.

5. The patient transport apparatus of claim 4, wherein the second state of the indicator is further defined as an absence of light emission via the light source.

6. The patient transport apparatus of claim 4, wherein the first state of the indicator is further defined as light emission via the light source at a first wavelength; and wherein the second state of the indicator is further defined as light emission via the light source at a second wavelength different from the first wavelength.

7. The patient transport apparatus of claim 1, wherein the indicator is further operable in a third state different from each of the first state and the second state; and wherein the controller is further configured to:

operate the indicator in the second state when the signal generated by the height sensor indicates that the litter is disposed in one of the plurality of lift configurations between the fully-retracted configuration and the transport configuration to communicate to the user that the litter is below the transport configuration, and operate the indicator in the third state when the signal generated by the height sensor indicates that the litter is disposed in one of the plurality of lift configurations between the transport configuration and the fully-extended configuration to communicate to the user that the litter is above the transport configuration.

8. The patient transport apparatus of claim 7, wherein the indicator comprises a light source;

wherein the first state of the indicator is further defined as light emission via the light source at a first wavelength;

wherein the second state of the indicator is further defined as light emission via the light source at a second wavelength different from the first wavelength; and wherein the third state of the indicator is further defined as light emission via the light source at a third wavelength different from each of the first wavelength and the second wavelength.

9. The patient transport apparatus of claim 1, wherein the input control comprises:

a first input control arranged for engagement by the user to move the litter toward the fully-extended configuration, and a second input control arranged for engagement by the user to move the litter toward the fully-retracted configuration.

10. The patient transport apparatus of claim 9, wherein the controller is further configured to:

drive the lift mechanism to move toward the fully-extended configuration in response to user engagement with the first input control, and drive the lift mechanism to move toward the fully-retracted configuration in response to user engagement with the second input control.

11. The patient transport apparatus of claim 10, wherein the user interface further comprises an automatic input control arranged for engagement by the user; and wherein the controller is further configured to drive the lift mechanism to move to the transport configuration in response to user engagement with the automatic input control.

12. The patient transport apparatus of claim 1, further comprising an auxiliary user interface operatively connected to the controller and comprising an auxiliary indicator operable between a first auxiliary state and a second auxiliary state different from the first auxiliary state.

13. The patient transport apparatus of claim 12, wherein the controller is further configured to:

operate the auxiliary indicator in the first auxiliary state when the signal generated by the height sensor corresponds to the transport signal value to communicate to the user that the litter is arranged in the transport configuration, and operate the auxiliary indicator in the second auxiliary state when the signal generated by the height sensor differs from the transport signal value to communicate to the user that the litter is arranged in one of the plurality of lift configurations other than the transport configuration.

14. The patient transport apparatus of claim 12, wherein the auxiliary user interface forms part of a portable electronic device carried by the user and disposed in wireless electrical communication with the controller.

15. The patient transport apparatus of claim 12, wherein the auxiliary user interface forms part of a wearable electronic device worn by the user and disposed in wireless electrical communication with the controller.

16. The patient transport apparatus of claim 12, wherein the auxiliary indicator comprises a haptic generator; and wherein the first auxiliary state of the auxiliary indicator is further defined as a haptic pulse via the haptic generator.

17. The patient transport apparatus of claim 1, wherein the indicator is further operable in a warning state different from each of the first state and the second state; and wherein the controller is further configured to operate the indicator in the warning state in response to the environment signal exceeding the environmental safety threshold and in response to the signal generated by the height sensor indicating that the litter is arranged higher than the environmentally-adjusted transport configuration.

18. The patient transport apparatus of claim 1, further comprising a patient sensor operatively connected to the controller and configured to generate a patient signal associated with a weight of the patient supported by the litter;
wherein the controller is further configured to:
compare the patient signal generated by the patient sensor against a weight safety threshold,
define a weight-adjusted transport configuration to position the litter at least partially lower than the transport configuration,
adjust the transport signal value and the predetermined threshold based on the weight-adjusted transport configuration, and
drive the lift mechanism to move to the weight-adjusted transport configuration in response to the patient signal exceeding the weight safety threshold and in response to the signal generated by the height sensor being within a predetermined threshold of the transport signal value upon user disengagement of the input control; and
wherein the controller is further configured to operate the indicator in a warning state, different from each of the first state and the second state, in response to the patient signal exceeding the weight safety threshold and in response to the signal generated by the height sensor indicating that the litter is arranged higher than the weight-adjusted transport configuration.

19. The patient transport apparatus of claim 1, further comprising an identification sensor to generate an identity signal associated with an identity of the user; and
wherein the controller is operably connected to the identification sensor and is further configured to:
compare the identity signal generated by the identification sensor against a list of users stored in the non-transitory storage medium to determine the identity of the user,
define a user-specific transport configuration to position the litter based on the identity of the user,
adjust the transport signal value and the predetermined threshold based on the user-specific transport configuration, and
drive the lift mechanism to move to the user-specific transport configuration in response to detection of the identity signal and in response to the signal generated by the height sensor being within a predetermined threshold of the transport signal value upon user disengagement of the input control.

20. A patient transport apparatus comprising:
a base;
a litter comprising a patient support surface to support a patient;
a lift mechanism to facilitate arranging the litter relative to the base between a plurality of lift configurations including a fully-retracted configuration, a fully-extended configuration, and a transport configuration between the fully-retracted configuration and the fully-extended configuration;
a user interface comprising an input control arranged for engagement by a user to operate the lift mechanism, and an indicator operable between a first state and a second state different from the first state;
a height sensor to generate a signal indicative of the arrangement of the patient support surface relative to the base between the plurality of lift configurations;
a patient sensor configured to generate a patient signal associated with a weight of the patient supported by the litter; and
a controller operably connected to the lift mechanism, the height sensor, and the user interface, the controller comprising one or more processors and a non-transitory storage medium having stored thereon instructions that when executed by the one or more processors are configured to:
compare the signal generated by the height sensor against a transport signal value associated with the transport configuration,
operate the indicator in the first state when the signal generated by the height sensor corresponds to the transport signal value to communicate to the user that the litter is arranged in the transport configuration,
operate the indicator in the second state when the signal generated by the height sensor differs from the transport signal value to communicate to the user that the litter is arranged in one of the plurality of lift configurations other than the transport configuration,
upon user engagement of the input control, drive the lift mechanism to move the litter relative to the base,
during movement of the litter relative to the base and in response to the signal generated by the height sensor being within a predetermined threshold of the transport signal value automatically drive the lift mechanism to move the litter to the transport configuration upon user disengagement of the input control,
compare the patient signal generated by the patient sensor against a weight safety threshold,
define a weight-adjusted transport configuration to position the litter at least partially lower than the transport configuration,
adjust the transport signal value and the predetermined threshold based on the weight-adjusted transport configuration,
drive the lift mechanism to move to the weight-adjusted transport configuration in response to the patient signal exceeding the weight safety threshold and in response to the signal generated by the height sensor being within a predetermined threshold of the transport signal value upon user disengagement of the input control, and
operate the indicator in a warning state, different from each of the first state and the second state, in response to the patient signal exceeding the weight safety threshold and in response to the signal generated by the height sensor indicating that the litter is arranged higher than the weight-adjusted transport configuration.

* * * * *